(12) United States Patent
Gross

(10) Patent No.: US 7,485,743 B2
(45) Date of Patent: Feb. 3, 2009

(54) OLIGOMERIC KETONE COMPOUNDS

(75) Inventor: Richard A. Gross, Brooklyn, NY (US)

(73) Assignee: BTG International Limited, London (GB)

(*) Notice: Subject to any disclaimer, the term of this patent is extended or adjusted under 35 U.S.C. 154(b) by 0 days.

(21) Appl. No.: 11/632,995

(22) PCT Filed: Jul. 19, 2005

(86) PCT No.: PCT/US2005/025369

§ 371 (c)(1),
(2), (4) Date: Feb. 13, 2007

(87) PCT Pub. No.: WO2006/020179

PCT Pub. Date: Feb. 23, 2006

(65) Prior Publication Data

US 2007/0197665 A1 Aug. 23, 2007

Related U.S. Application Data

(60) Provisional application No. 60/588,990, filed on Jul. 20, 2004.

(51) Int. Cl.
C07C 69/66 (2006.01)
A61K 31/215 (2006.01)
A61K 31/12 (2006.01)
A61K 47/00 (2006.01)

(52) U.S. Cl. .................. 560/174; 560/185; 514/529; 514/675; 424/439

(58) Field of Classification Search ............. 560/174, 560/185; 514/529, 675; 424/439
See application file for complete search history.

(56) References Cited

U.S. PATENT DOCUMENTS

| | | | |
|---|---|---|---|
| 3,284,298 A | 11/1966 | Hajime et al. | |
| 4,067,999 A | 1/1978 | Glabe et al. | |
| 4,211,846 A | 7/1980 | Lafferty | |
| 4,234,599 A | 11/1980 | Van Scott et al. | |
| 4,346,107 A | 8/1982 | Cavazza et al. | |
| 4,351,835 A | 9/1982 | Stanko | |
| 4,363,815 A | 12/1982 | Yu et al. | |
| 4,579,955 A | 4/1986 | Lammerant et al. | |
| 4,701,443 A | 10/1987 | Nelson et al. | |
| 4,771,074 A | 9/1988 | Lammerant et al. | |
| 4,929,449 A | 5/1990 | Veech | |
| 4,970,143 A | 11/1990 | Guidoux et al. | |
| 4,983,766 A | 1/1991 | Imwinkelried et al. | |
| 4,997,976 A | 3/1991 | Brunengraber et al. | |
| 5,100,677 A | 3/1992 | Veech | |
| 5,116,868 A | 5/1992 | Chen et al. | |
| 5,126,373 A | 6/1992 | Brunengraber et al. | |
| 5,200,200 A | 4/1993 | Veech | |
| 5,286,842 A | 2/1994 | Kimura ............ 528/353 | |
| 5,292,774 A | 3/1994 | Hiraide et al. | |
| 5,348,979 A | 9/1994 | Nissen et al. | |
| 5,654,266 A | 8/1997 | Chen et al. | |
| 5,693,850 A | 12/1997 | Birkhahn et al. | |
| 5,719,119 A | 2/1998 | Veech | |
| 5,912,269 A | 6/1999 | Tung | |
| 6,136,862 A * | 10/2000 | Hiraide et al. ............. 514/578 |
| 6,207,217 B1 | 3/2001 | Peoples et al. ............. 426/635 |
| 6,207,856 B1 * | 3/2001 | Veech .................. 560/178 |
| 6,232,345 B1 | 5/2001 | Hiraide et al. | |
| 6,323,237 B1 | 11/2001 | Veech | |
| 6,380,244 B2 * | 4/2002 | Martin et al. ............. 514/449 |
| 6,384,252 B1 | 5/2002 | Pageat | |
| 6,835,750 B1 | 12/2004 | Henderson | |
| 2002/0132846 A1 | 9/2002 | Stone | |
| 2004/0266872 A1 | 12/2004 | Veech | |

FOREIGN PATENT DOCUMENTS

| | | |
|---|---|---|
| EP | 0108820 | 11/1982 |
| EP | 0288908 | 4/1988 |
| EP | 0318357 | 11/1988 |
| EP | 0466050 | 7/1991 |
| EP | 0562188 | 3/1992 |
| EP | 0552896 | 1/1993 |
| EP | 0780123 | 11/1996 |

(Continued)

OTHER PUBLICATIONS

International Preliminary Report on Patentability; International Application No. PCT/US2005/025369; International Filing Date Jul. 19, 2005 (5 pgs).
Co-pending U.S. Appl. No. 10/763,393, filed Jan. 26, 2004.
*Accera, Inc. Enters into Product Development Agreement with Nestle Purina PetCare Global Resources, Inc.*; Copyright 2007 Accera, Inc.; Posted on Jan. 8, 2007 (1 pg).
*Accera Initiates Phase 2 Trial in Age Associated Memory Impairment*; Accera, Inc.; Posted on Aug. 23, 2006 (2 pgs).
*Accera, Inc. to Present at Upcoming Investor Conferences*; Accera, Inc.; Posted on May 8, 2007 (2 pgs).
*Accera, Inc. Announces Results of Phase II Study in Alzheimer's Disease American Academy of Neurology Meeting*; Posted on May 4, 2007 (2 pgs).

(Continued)

*Primary Examiner*—Sikarl A Witherspoon
(74) *Attorney, Agent, or Firm*—Nixon & Vanderhye

(57) ABSTRACT

A novel keto8enic compound is provided having general: Formula R(OCH(CH$_3$)CH$_2$C(O))$_n$—O-A wherein n is an integer of 3 to 10, A is the residue of a 3-keto alkan-1-ol and R is selected from the group consisting of H, C1-C6 alkyl and acetoacetyl- Preferred compounds are those wherein A is a residue is of 4-hydroxy-2 butanone. A particularly preferred compound is a 4-hydroxy-2-butanone ester of an R-3-hydroxybutyrate oligomer having general: Formula H(OCH(CH$_3$)CH$_2$C(O))$_n$—O—CH$_2$—CH$_2$—(CO)—CH$_3$ Nutraceutical and pharmaceutical compositions are provided for use in treating one or more of acute trauma, hemorrhagic shock, neurodegeneration, diabetes, and epilepsy, stroke, head trauma, myocardial infraction, congestive heart failure, pulmonary failure, kidney failure, obesity depression, pain and impaired cognition.

14 Claims, 4 Drawing Sheets

FOREIGN PATENT DOCUMENTS

Figure 1:
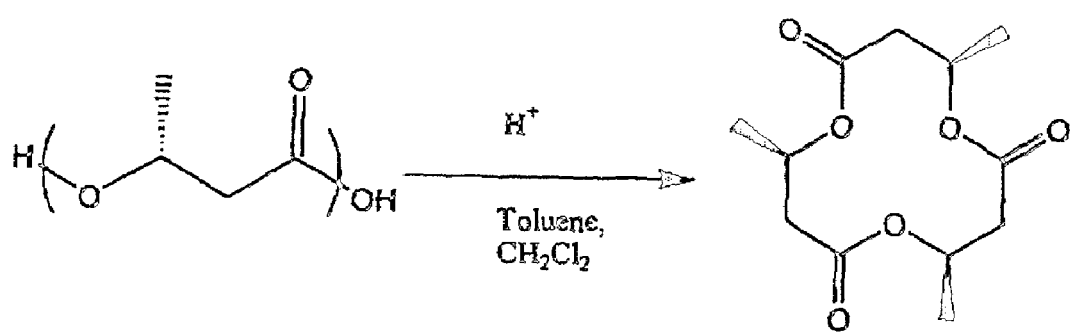

| | | |
|---|---|---|
| EP | 1 188 437 A | 3/2002 |
| FR | 2 531 859 A1 | 2/1984 |
| GB | 1 476 624 A | 6/1977 |
| GB | 2126082 | 8/1982 |
| WO | WO 92/09210 | 11/1991 |
| WO | WO 92/09211 | 11/1991 |
| WO | WO 98/41201 | 3/1998 |
| WO | WO 98/51812 | 5/1998 |
| WO | WO 98/41200 A | 9/1998 |
| WO | WO 99/34687 | 1/1999 |
| WO | WO 00/15216 | 3/2000 |
| WO | WO 00/15216 A | 3/2000 |
| WO | WO 00/28985 A | 5/2000 |
| WO | WO 01/82928 A1 | 11/2001 |
| WO | WO 02/062327 A | 8/2002 |
| WO | WO 02/102363 A | 12/2002 |
| WO | WO 2004/077938 A2 | 9/2004 |
| WO | WO 2004/108740 A | 12/2004 |
| WO | WO 2005/034874 A | 4/2005 |
| WO | WO 2005/086619 A | 9/2005 |
| WO | WO 2007/001883 A2 | 1/2007 |

OTHER PUBLICATIONS

Reger, M.A., et al; "Effects of beta-hydroxybutyrate on cog . . . impaired adults"; *PubMed Abstract, Neurobiol Aging*; Mar. 2004; 25(3):311-4; Accera, Inc., Aurora, CO, USA, (2 pgs).

Bo Chen, Jun Hu, Elizabeth M. Miller, Wenchun Xie, Minmin Cai, and Richard A. Gross, Candida antarctica Lipase B Chemically Immobilized on Epoxy-Activated Micro- and Nanobeads: Catalysts for Polyester Synthesis *Biomacromolecules*, 9, 463-471(2008).

Bo Chen, Elizabeth M. Miller, Lisa Miller, John J. Maikner, and Richard A. Gross, Effects of Macroporous Resin Size on *Candida antarctica* Lipase B Adsorption, Fraction of Active Molecules, and Catalytic Activity for Polyester Synthesis *Langmuir*, 23, 1381-1387(2007).

Mo Hunsen, Abul Azim, Harald Mang, Sabine R. Wallner, Asa Ronkvist, Wenchun Xie, and Richard A. Gross, A Cutinase with Polyester Synthesis Activity *Macromolecules*, 40(2), 148-150(2007).

Dodds, D. R.; Gross, R. A., Chemicals from biomass, *Science*, 318 (5854), 1250-1251 (2007).

Sharma, B.; Azim, A.; Azim, H.; Gross, R. A., Enzymatic Synthesis and solid-state properties of aliphatic polyesteramides with polydimethylsiloxane blocks. *Macromolecules*, 40(22), 7919-7927(2007).

Jiang, Z. Z.; Liu, C.; Xie, W. C.; Gross, R. A., Controlled lipase-catalyzed synthesis of poly(hexamethylene carbonate). *Macromolecules*, 40 (22), 7934-7943 (2007).

Hardin, R.; Pierre, J.; Schulze, R.; Mueller, C. M.; Fu, S. L.; Wallner, S. R.; Stanek, A.; Shah, V.; Gross, R. A.; Weedon, J.; Nowakowski, M.; Zenilman, M. E.; Bluth, M. H., Sophorolipids improve sepsis survival: Effects of dosing and derivatives. *Journal of Surgical Research*, 142 (2), 314-319 (2007).

Fu, S. L.; Mueller, C.; Lin, Y. Y.; Viterbo, D.; Pierre, J.; Shah, V.; Gross, R.; Schulze, R.; Zenilman, M., Sophorolipid treatment decreases LIPS induced inflammatory responses and no production in macrophages. *Journal of the American College of Surgeons*, 205 (3), S44-S44 (2007).

Jiang, Z. Z.; Azim, H.; Gross, R. A.; Focarete, M. L.; Scandola, M., Lipase-catalyzed copolymerization of omega-pentadecalactone with p-dioxanone and characterization of copolymer thermal and crystalline properties. *Biomacromolecules*, 8 (7), 2262-2269 (2007).

Kulshrestha, A. S.; Gao, W.; Fu, H. Y.; Gross, R. A., Synthesis and characterization of branched polymers from lipase-catalyzed trimethylolpropane copolymerizations. *Biomacromolecules*, 8 (6), 1794-1801 (2007).

Chen, B.; Miller, M. E.; Gross, R. A., Effects of porous polystyrene resin parameters on *Candida antarctica* Lipase B adsorption, distribution, and polyester synthesis activity. *Langmuir*, 23 (11), 6467-6474 (2007).

Hagler, M.; Smith-Norowitz, T. A.; Chice, S.; Wallner, S. R.; Viterbo, D.; Mueller, C. M.; Gross, R.; Nowakowski, M.; Schulze, R.; Zenilman, M. E.; Bluth, M. H., Sophorolipids decrease IgE production in U266 cells by downregulation of BSAP (Pax5), TLR-2, STAT3 and IL-6. *Journal of Allergy and Clinical Immunology*, 119 (1), S263-S263 (2007).

Felse, P. A.; Shah, V.; Chan, J.; Rao, K. J.; Gross, R. A., Sophorolipid biosynthesis by *Candida bombicola* from industrial fatty acid residues. *Enzyme and Microbial Technology*, 40 (2), 316-323 (2007).

Wei Gao, Rena Hagver, Vishal Shah, Wenchun Xie, Richard A. Gross, M. Firat Ilker, Chrissy Bell, Kelly A. Burke, and E. Bryan Coughlin Glycolipid Polymer Synthesized from Natural Lactonic Sophorolipids by Ring-Opening Metathesis Polymerization *Macromolecules*, 40(2), 145(2006).

Li, Geng; Vaidya, A; Viswanathan, K; Cui, Jr; Xie, W.C.; Gao, W; Gross, R.A.; Rapid regioselective oligomerization of L-glutamic acid diethyl ester catalyzed by papain, *Macromolecules* 39 (23): 7915-7921 (2006).

Bluth, M.H.; Kandil, E; Mueller, C.M.; Shah, V.; Lin, Y.Y.; Zhang, H; Dresner, L.; Lempert, L.; Nowakowski, M.; Gross, R; Schulze, R.; Zenilman, M.E. Sophorolipids block lethal effects of septic shock in rats in a cecal ligation and puncture model of experimental sepsis, *Critical Care Medicine* 34 (1): 188-195 (2006).

Sahoo, B; Bhattacharya, A.; Fu, H.Y.; Gao, W.; Gross, R.A. Influence of PEG end-group and molecular weight on its reactivity for lipase-catalyzed polyester synthesis *BioMacromolecules* 7 (4): 1042-1048 (2006).

Mueller, C.M.; Viterbo, D.; Murray, P.J.; Shah, V.; Gross, R.; Schulze, R.; Zenilman, M.E.; Bluth, M.H. Sophorolipid treatment decreases inflammatory cytokine expression in an in vitro model of experimental sepsis. *Faseb Journal* 20 (4): A204-A204 Part 1, (2006).

Shah, V.; Baldrian, P.; Eichlerova, I.; Dave, R.; Madamwar, D.; Nerud, F.; Gross, R. Influence of dimethyl sulfoxide on extracellular enzyme production by *Pleurotus ostreatus*. *Biotechnology Letters* 28 (9): 651-655 (2006).

Hu, J; Gao, W.; Kulshrestha, A.; Gross, R.A. "Sweet polyesters": Lipase-catalyzed condensation—Polymerizations of alditols, *Macromolecules* 39 (20): 6789-6792 (2006).

Azim, A; Shah, V.; Doncel, G.F.; Peterson, N.; Gao, W.; Gross, R. Amino acid conjugated sophorolipids: A new family of biologically active functionalized glycolipids. *Bioconjugate Chemistry* 17 (6): 1523-1529 (2006).

Azim, H.; Dekhterman, A.; Jiang, Z.Z.; Gross, R.A. Candida antarctica lipase B-catalyzed synthesis of poly(butylene succinate): Shorter chain building blocks also work, *BioMacromolecules* 7 (11): 3093-3097 (2006).

Shah V, Doncel GF, Seyoum T, Eaton KM, Zalenskyaya I, Hagver R, Azim A, Gross R. Sophorolipids, microbial glycolipids with anti-human immunodeficiency virus and sperm-immobilizing activities. *Antimicrob Agents Chemother*; 149; 1-8 (2005).

Mijovic, J.; Bian, Y.; Gross, R. A.; Chen, B. Dynamics of Proteins in Hydrated State and in Solution As Studied by Dielectric Relaxation Spectroscopy *Macromolecules*; 38(26) 10812-10819 (2005).

Chakraborty. S,Sahoo. B,Teraoka, Gross.RA Solution properties of starch nanoparticles in water and DMSO as studied by dynamic light scattering *Carbohydrates polymers*; 60(4); 475-481, (2005).

Nakaoki, T.; Mei, Y.; Miller, L.-M.; Kumar, A; Kalra, B; Miller, E.-M.; Kirk, O.; Christensen, M.; Gross, R.A. "Candida antartica Lipase B catalyzed polymerization of lactones: Effects of immobilization matrices on polymerization kinetics and Molecular Weight" *Industrial Biotechnology*; 1(2) 126-134 (2005).

Sahoo, B.; Brandstadt, K. F.; Lane, T. H.; Gross, R. A. "Sweet Silicones": Biocatalytic Reactions to Form Organosilicon Carbohydrate Macromers *Org. Lett.*; 7(18); 3857-3860 (2005).

Loos, K.; Kennedy, S. B.; Eidelman, N.; Tai, Y.; Zharnikov, M.; Amis, E. J.; Ulman, A.; Gross, R. A. Combinatorial Approach To Study Enzyme/Surface Interactions *Langmuir*; 21(12); 5237-5241 (2005).

Kulshrestha, A. S.; Sahoo, B., Gao, W.; Fu, H. and Gross, R.A. "Lipase Catalysis. A Direct Route to Linear Aliphatic Copolyesters of Bis(hydroxymethyl)butyric Acid with Pendant Carboxylic Acid Groups", *Macromolecules*; 38(8); 3205-3213 (2005).

Kulshrestha, A. S.; Gao, W.; Gross, R.A. "Glycerol Copolyesters: Control of Branching and Molecular Weight Using a Lipase Catalyst", *Macromolecules*, (2005); 38(8); 3193-3204.

Ceccorulli, G.; Scandola, M.; Kumar, A.; Kalra, B.; Gross, R. A., "Cocrystallization of Random Copolymers of—Pentadecalactone and -Caprolactone Synthesized by Lipase Catalysis" *BioMacromolecules*; 6(2); 902-907 (2005).

Chakraborty, S.; Sahoo, B.; Teraoka, I.; Miller, L. M.; Gross, R. A. "Enzyme-Catalyzed Regioselective Modification of Starch Nanoparticles" *Macromolecules*; 38(1); 61-68 (2005).

Zhang, L., Somasundaran, P., Singh, S. K., Felse, A. P., Gross, R.A. Synthesis and interfacial properties of sophorolipid derivatives *Colloids and Surfaces A: Physiochem.Eng. Aspects*; 240; 75-82 (2004).

Zhou, S., Xu, Chang., Wang, J., Gao, W., Akhverdiyeva., Shah, V., Gross, R. A. Supramolecular Assembles of a Naturally Derived Sopholipid. *Langmuir*; 20; 7926-7932 (2004).

Kalra, B.; Kumar, A.; Gross, R. A.; Baiardo, M.; Scandola, M. "Chemoenzymatic Synthesis of New Brush Copolymers Comprising Poly( -pentadecalactone) with Unusual Thermal and Crystalline Properties" *Macromolecules*; 37(4); 1243-1250 (2004).

Mahapatro, A.; Kumar, A.; Kalra, B.; Gross, R. A. "Solvent-Free Adipic Acid/1,8-Octanediol Condensation Polymerizations Catalyzed by *Candida antartica* Lipase B" *Macromolecules*; 37(1); 35-40 (2004).

Van As, B. A. C.; Thomassen, P.; Kalra, B.; Gross, R. A.; Meijer, E. W.; Palmans, A. R. A.; Heise, A. "One-Pot Chemoenzymatic Cascade Polymerization under Kinetic Resolution Condiditions" *Macromolecules*; 37(24); 8973-8977 (2004).

Mahapatro, A.; Kumar, A.; Gross, R. A.; "Mild, Solvent-Free -Hydroxy Acid Polycondensations Catalyzed by *Candida antarctica* Lipase B." *BioMacromolecules*; 5(1); 62-68 (2004).

Loeker, F. C.; Duxbury, C. J.; Kumar, R.; Gao, W.; Gross, R. A.; Howdle, S. M. Enzyme-Catalyzed Ring-Opening Polymerization of -Caprolactone in Supercritical Carbon Dioxide. *Macromolecules*; 37(7); 2450-2453 (2004).

Hyung-Pil, S, Chung, C.H., Kim, S.K., Gross, R.A., Kaplan., D.L. Lee, J.W. Mass Production of Pullulan with Optimized Concentrations of Carbon and Nitrogen sources by *Aureobasidium pullulans* HP-2001 in a 100-L Bioreactor J. Microbol. Biotechnol.; 14,(2), 237-242 (2004).

Mei, Y., Kumar, A, Gao, W, Gross, R.A., Kennedy, S.B., Washburn, N.R., Amis, E,.J., Elliot, John T. Biocompatibility of sorbitol-containing polyesters. Part 1: Synthesis, surface analysis and cell response in vitro; *Biomaterials*; 25; 4195-4201 (2004).

Singh, S,K, Felse,, A. P., Nunez, A., Foglia, T.A. and Gross, R.A. Regioselective Enzyme-Catalyzed Synthesis of Sophorolipid Esters, Amides and Multifunctional Monomers. *J. Org. Chem.*; 68; 5466-5477 (2003).

Kumar, A.; Kulshrestha, A. S.; Gao, W.; Gross, R. A.; Versatile Route to Polyol Polyesters by Lipase Catalysis *Macromolecules*; 36(22); 8219-8221 (2003).

Mei, Y.; Miller, L.; Gao, W.; Gross, R. A.; Imaging the Distribution and Secondary Structure of Immobilized Enzymes Using Infrared Microspectroscopy *BioMacromolecules*; 4(1); 70-74 (2003).

Mahapatro, A.; Kalra, B.; Kumar, A.; Gross, R. A.; Lipase-Catalyzed Polycondensations: Effect of Substrates and Solvent on Chain Formation, Dispersity, and End-Group Structure *BioMacromolecules*; 4(3); 544-551 (2003).

Fu, H.; Kulshrestha, A. S.; Gao, W.; Gross, R. A.; Baiardo, M.; Scandola, M., Physical Characterization of Sorbitol or Glycerol Containing Aliphatic Copolyesters Synthesized by Lipase-Catalyzed Polymerization *Macromolecules*; 36(26); 9804-9808 (2003).

Dyal, A., Loos, Katja., Noto, M., Chang, S.W., Spagnoli, C., Shafi, Kurikka V.P.M., Ulman, A., Cowman,M.,Gross. R.A. Activity of *Candida rugosa* Lipase -Fe2O3 Magnetic NanoparticlesγImmobolized on *J. Am. Chem. Soc.*; 125; 1684-1685 (2003).

Mei, Y, Kumar, A, Gross; R.A., "Kenetics and Mechanism of *Candida antarctica* Lipase B Catalyzed Solution Polymerization of -Caprolaction", *Macromolecules*; 36(15); 5530-5536 (2003).

Gross, R. A., Kalra, B; "Biodegradable Polymers for the Environment", *Science*, 297, 803-806 (2002).

Focarete, M. L.; Gazzano, M.; Scandola, M.; Kumar, A.; Gross, R. A.; -Pentadecalactone and Trimethylene Carbonate from Lipaseω"Copolymers of Catalysis: Influence of Microstructure on Solid-State Properties", *Macromolecules*; 35(21); 8066-8071, (2002).

Kumar, A.; Gross, R. A.; Wang, Y.; Hillmyer, M. A.; "Recognition by Lipases -Hydroxyl Macroinitiators for Diblock Copolymer Synthesis"ωof *Macromolecules*; 35(20); 7606-7611, (2002).

Kumar, R.; Gao, W.; Gross, R. A.; "Functionalized Polylactides: Preparation and Characterization of [L]-Lactide-co-Pentofuranose" *Macromolecules*; 2002; 35(18); 6835-6844.

Bankova, M.; Kumar, A.; Impallomeni, G.; Ballistreri, A.; Gross, R. A.; -caprolactone) Transesterificatione"Mass-Selective Lipase-Catalyzed Poly( Reactions", *Macromolecules*; 35(18); 6858-6866, (2002).

Hu, Shanghui; Gupta, Pankaj; Prasad, Ashok K.; Gross, Richard, A., Parmar, Virinder S. "Selective enzymatic epoxidation of dienes: Generation of Functional Enantiomerically Enriched Diene Monoepoxy Monomers", *Tetrahedron Letters*; 43; 6763-6766 (2002).

B. Kalra and R.A. Gross, "HRP-Mediated Polymerizations of acrylamide and sodium acrylate", *Green Chemistry*; 4; 174-178 (2002).

Y. Mei, A. Kumar, and Richard A. Gross, "Probing Water-Temperature Relationships for Lipase-Catalyzed Lactone Ring-opening Polymerizations" *Macromolecules*; 35, 5444-5448 (2002).

R. Kumar and R.A. Gross, Biocatalytic Route to Well-Defined Macromers Built around a Sugar Core, *J. Am. Chem. Soc.*, 124(9): 1850-1851 (2002).

V Guilmanov, A Ballistreri, G Impallomeni, R.A. Gross, "Oxygen Transfer Rate and Sophorose Lipid Production by *Candida bombicola"*, *Biotechnol. and Bioeng*; 77(5), 489-494 (2002).

R. A. Gross, A Kumar, B Kalra, "In-vitro Enzyme Catalyzed Polymer Synthesis", *Chemical Reviews*, 101(7), 2097-2124 (2001).

J.W. Lee, F. Dang, W.G. Yeomans, A.L. Allen, R.A. Gross, D.L. Kaplan, Acetobacter xylinium ATCC 10245: Production of Chitosan-Cellulose and Chitin-Cellulose Exopolymers, *Applied and Environmental Microbiology*, 67(9), 3970-3975 (2001).

M. L. Focarete, A. Kumar, M. Scandola, R. A. Gross, "Physical Characterization of Poly(w-pentadecalactone) Synthesized by Lipase-Catalyzed Ring-Opening Polymerization", *J of Polymer Science, Part B: Polymer Physics*, 39(15), 1721-1729 (2001).

R.A.Gross, B.Kalra, A. Kumar "In-vitro Lipase Catalyzed Polyester and Polycarbonate Synthesis" *Applied Microbiology and Biotechnology*; 55(6), 655-660 (2001).

A Kumar, K Garg, R. A. Gross, "Lipase-Catalyzed Copolymerizations of Trimethylene Carbonate and w-Pentadecalactone" *Macromolecules*; 34; 3527-3533 (2001).

A Kumar, R.A Gross, "Lipase-Catalyzed Transesterification: New Synthetic Routes To Copolyesters", *J. Am. Chem. Soc.*; 122; 11767-11770 (2000).

A Kumar, B Kalra, A Dekhterman, R. A. Gross, "Efficient Ringopening -Pentadecalactoneω-Caprolactone and εPolymerization and Co-polymerization of Catalyzed by *Candida antartica* Lipase B", *Macromolecules*, 33, 6303-6309 (2000).

K.S. Bisht, W Gao, R.A. Gross, "Glycolipids from *Candida Bombicola*: Polymerization of 6-O-Acryl Sophorolipid Derivative", *Macromolecules*, 33, 6208-6210 (2000).

A. Kumar, R.A.Gross, J.D.Jenderoseck, "Poly(3-hydroxybutrate)-depolymerase from *Pseudomonas lemoignei*: catalysis of esterification in organic media" *Journal of Organic Chemistry*, 65, 7800-7806 (2000).

B Kalra, R.A. Gross, "HRP-Mediated Free Radical Polymerization of Methyl Methacrylate", *BioMacromolecules*, 1, 501-505 (2000).

A Kumar and R.A. Gross, *Candida antartica* Lipase B Catalyzed Polycaprolactone Synthesis: Effects of Organic Media and Temperature, *BioMacromolecules*, 1, 133-138 (2000).

J.W. Lee, W.G. Yeomans, A.L. Allen, F. Deng, R.A. Gross and D.L. Kaplan, "Biosynthesis of Novel Exopolymers by *Aureobasidium pullulans"*, *Appl. & Env. Microbiol.* 65(12), 5265-5271 (1999).

A. Gorkovenko, J. Zhang, R. A. Gross, D. L. Kaplan, A. L. Allen. Control of unsaturated fatty acid substituents in emulsans. *Carbohydrate Polymers*. 39, 79-84 (1999).

R. D. Ashby, F.-Y. Shi and R.A. Gross, "A Tunable Switch to Regulate the Synthesis of Low and High Molecular Weight Microbial Polyesters" *Biotechnology and Bioengineering*, vol. 62 (1), (1999).

K. Bisht, R. Gross and D. Kaplan, "Enzyme-Mediated Regioselective Acylations of Sophorolipids", *J. Org. Chem.*, 64:3, 780-789 (1999).

X. Chen and R. Gross, "Versatile Copolymers from [L]-Lactide and [D]-Xylofuranose", *Macromolecules*, 32, 308-314 (1999).

K. S. Bisht, F. Deng, R. A. Gross, D. L. Kaplan and G. Swift, "Ethyl Glucoside as a Multifunctional Initiator for Enzyme-Catalyzed regioselective Lactone Ring-opening Polymerization" *J. Am. Chem. Soc.*, vol. 120, 1363-1367 (1998).

K. S. Bisht, R. A. Gross and A. L. Cholli, "Enzymatic Polymerization of -CL) Containing an Ethyl Glucopyranoside Head Group: An NMR Study"εPoly( *Applied Spectroscopy*, 52 (11) 1472-1478, (1998).

Young Ko and Richard A. Gross -Poly(glutamic acid) Formation by Bacillusγ, "licheniformis ATCC 9945a: Physiological Effects of glucose and glycerol", *Biotechnol. and Bioeng.*, 57(40), 430-437 (1998).

D. L. Kaplan, J. Dordick, R. A. Gross, G. Swift. In Enzymes in Polymer Science, R. Gross, D. Kaplan, G. Swift, Editors; *American Chemical Society Symposium Series* 684: 2-17 (1998).

Kirpal S. Bisht, Lori A. Henderson, Yuri Y. Svirkin and Richard A. Gross, David L. Kaplan and Graham Swift, "Monomer and Polymer Synthesis by Lipase-Catalyzed Ring-Opening Reactions", In, *Enzymes in Polymer Synthesis*, Eds. R.A. Gross, D.L. Kaplan and G. Swift, ACS Symposium Series 684, ACS, Washington, 90-111 (1998).

Xianhai Chen, Stephen P. McCarthy and Richard A. Gross, Preparation and Characterization of Polycarbonates from 2,4,8,10-Tetraoxaspiro[5,5]undecane-3-one (DOXTC)-Trimethylenecarbonate (TMC) Ring-Opening Polymerizations, *J. Appl. Polym. Sci.*, vol. 67, 547-557 (1998).

Xianhai Chen, Stephen P. McCarthy and Richard A. Gross, "Synthesis, Characterization and Epoxidaion of an Aliphatic Polycarbonate from 2,2-[4,4-cyclohexene-1]-trimethylene tcarbonate (cHTC) Ring-Opening Polymerization", *Macromolecules*; 30, 3470-3476 (1997).

Fengying Shi, Richard D. Ashby and Richard A. Gross, "Formation by Alcaligenes species of Microbial Polyesters Containing 3-Hydroxybutyrate and 4-Hydroxybutyrate Repeat Units: Investigation of Product Homogeneity", *Macromolecules*, vol. 30, 2521-2523 (1997).

Richard Ashby, Feng-Ying Shi, and Richard A. Gross, "Use of poly(ethylene glycol) to control the end group structure and molecular weight of poly(3-hydroxybutyrate) formed by *Alcaligenes latus* DSM 1122," *Tetrahedron*, vol. 53, No. 45, 15209-115223 (1997).

Kirpal S. Bisht, Yuri Y. Svirkin, Lori A. Henderson, Richard A. Gross, David L. Kaplan and Graham Swift, Lipase-Catalyzed Ring-Opening Polymerization of Trimethylene Carbonate, *Macromolecules*, vol. 30, 7735-7742 (1997).

Jin W. Lee, Water G. Yeomans, Alfred L. Allen, David L. Kaplan, and Richard A. Gross, "Microbial production of water-soluble non curdlan type exopolymer-B with controlled composition by *Agrobacterium* sp. ATCC 31749" *Biotechnol. Lett.*, 19(12), 1217-1221 (1997).

Jin W. Lee, Water G. Yeomans, Alfred L. Allen, David L. Kaplan, and Richard A. Gross. "Production of zoogloea gum by *Zoogloea ramigera* with glucose analogs" *Biotechnol. Lett.* 19(8), 799-802 (1997).

Kirpal S. Bisht, Lori A. Henderson, Richard A. Gross, David L. Kaplan and Graham Swift, "Enzyme-Catalyzed Ring-Opening Polymerization of -pentadecalactone)",ωPoly( *Macromolecules*, vol. 30, 2705-2711 (1997).

Jin W. Lee, Water G. Yeomans, Alfred L. Allen, David L. Kaplan, Frank Deng, and Richard A. Gross. Exopolymers from curdlan production-incorporation of glucose-related sugars by *Agrobacerium* sp. ATCC 31749. *Can. J. Microbiol.* 43:149-156. (1997).

Jinwen Zhang, Alexander Gorkovenko, Richard A. Gross, Alfred L. Allen and David L. Kaplan Incorporation of 2-Hydroxyl Fatty Acids by *Acinetobacter calcoaceticus* RAG-1 to Tailor Emulsan Structure, *Intern. J. Biol. Macromol.*,vol. 20, 9-21 (1997).

Alexander Gorkovenko, Jinwen Zhang, Richard A. Gross, Alfred L. Allen and David L. Kaplan, "Bioengineering of Emulsifier Structure: Emulsan Analogs", *Can. J. Microbiol*, vol. 43, 384-390 (1997).

Renée T. Macdonald, Stephen P. McCarthy and Richard A. Gross, "Enzymatic Degradability of Poly(lactide): Effects of Chain Stereochemistry and Material Crystallinity", *Macromolecules*, vol. 29, 7356-7361 (1996).

Lori A. Henderson, Yuri, Y. Svirkin, Richard A. Gross, David L. Kaplan and -caprolactone: Effects ofεGraham Swift, "Enzyme Catalyzed Polymerizations of Initiator on Product Structure, Propagation Kinetics, and Mechanism", *Macromolecules*, vol. 29, 7759-7766 (1996).

David S. Roesser, Stephen P. McCarthy, Richard A. Gross and David L. Kaplan, "Effects of Substitution Site on Acetyl Amylose Biodegradability by Amylase Enzymes", *Macromolecules*, vol. 29, No. 1, 1-9 (1996).

Feng-Ying Shi, Richard Ashby and Richard A. Gross, "Use of Poly(ethylene glycol)s to Regulate Poly(3-hydroxybutyrate) Molecular Weight during *Alcaligenes eutrophus* Cultivations", *Macromolecules*, vol. 29, 7753-7758 (1996).

Feng-Ying Shi, Denise Rutherford and Richard A. Gross, "Microbial Polyester Synthesis: Effects of Poly(ethylene glycol) on Product Composition, Repeat Unit Sequence and End Group Structure", *Macromolecules*, vol. 29, 10-17 (1996).

Richard A. Gross, Oh-young Kim, Denise R. Rutherford and Richard A. Newmark, "Cyanophenoxy-Containing Microbial Polyesters: Structural Analysis, Thermal Properties, Second Harmonic Generation and In-Vivo Biodegradability", *Polym. International*, vol. 39, 205-213 (1996).

Jin Xu, Stephen P. McCarthy and Richard A. Gross, "Racemic -propiolactone Polymerization by Organometallic Catalyst Systems",β-Methyl-α *Macromolecules*, vol. 29, No. 13, 4565-4571 (1996).

Anne-Marie Cromwick, Gregory A. Birrer and Richard A. Gross, "Effects of pH -Poly(glutamic acid) Formation by *Bacillus licheniformis* inγand Aeration on Controlled Batch Fermenter Cultures", *Biotechnol. Bioeng.*, vol. 50, 222-227 (1996).

Oh-young Kim, Richard A. Gross, W. James Hammar and Richard A. Newmark, -hydroxyalkanoates) Containing Fluorinatedβ"Microbial Synthesis of Poly( Side-Chain Substituents", *Macromolecules*, vol. 29, No. 13, 4572-4581 (1996).

Jin Xu, Richard A. Gross, David L. Kaplan and Graham Swift, "Chemoenzymatic -propiolactone) Stereocopolymers",β-methyl-αSynthesis and Study of Poly( *Macromolecules*, vol. 29, No. 13, 4582-4590 (1996).

Jin Xu, Richard A. Gross, David L. Kaplan and Graham Swift, "Chemoenzymatic Route to Poly(3-hydroxybutyrate)", *Macromolecules*, vol. 29, 3856-3861 (1996).

Jin Xu, Stephen P. McCarthy, Richard A. Gross and David L. Kaplan "Chitosan Film Acylation and Effects on Biodegradability", *Macromolecules*, vol. 29, 3436-3440 (1996).

Yuri Y. Svirkin, Jin Xu, Richard A. Gross, David L. Kaplan and Graham Swift, "Enzyme-Catalyzed Stereoselective Ring-Opening Polymerization of -propiolactone",β-Methyl-α *Macromolecules*, vol. 29, No. 13, 4591-4597 (1996).

Zbigniew Jedlinski, Marek Kowalczuk, Piotr Kurcok, Grazyna Adamus, Andrzej Matuszowicz, Wanda Sikorska, Richard A. Gross, Jin Xu, and Robert W. Lenz, -Butyrolactoneβ"Stereochemical Control in the Anionic Polymerization of Initiated with Alkali-Metal Alkoxides", *Macromolecules*, vol. 29, 3773-3777 (1996).

Oh-young Kim, Richard A. Gross and Denise R. Rutherford, "Bioengineering of -hydroxyalkanoates) for Advanced Material Applications: Incorporation ofβPoly( Cyano- and Nitrophenoxy Side Chain Substituents", *Can. J. Microbiol.*, vol. 41, supplement 1, 32-43 (1995).

Ferdinando F. Bruno, Joseph A. Akkara, Madhu Ayyagari, David L. Kaplan, Richard A. Gross, Graham Swift and Jonathan S. Dordick, "Enzymatic Modification of Insoluble Amylose in Organic Solvents", *Macromolecules*, vol. 28, 8881-8883 (1995).

Renée T. Macdonald, Satich K. Pulapura, Yuri Y. Svirkin and Richard A. Gross, -Caprolactone Ring-Opening Polymerization",ε"Enzyme Catalyzed *Macromolecules*, 28, 73-78 (1995).

Anne-Marie Cromwick and Richard A. Gross, Effects of Manganese (II) on -Poly(glutamic acid)γ*Bacillus licheniformis* ATCC 9945A Physiology and Formation, *Int. J. Biol. Macromol.*, vol. 17, No. 5, 259-267 (1995).

Anne-Marie Cromwick and Richard A. Gross, Investigation by NMR of Metabolic -Poly(Glutamic Acid) Using 13C Labeled Citrate andγRoutes to Bacterial Glutamate as Media Carbon sources, *Can. J. Microbiol.*, vol. 41: 902-909 (1995).

Richard A. Gross, Ji-Dong Gu, David Eberiel and Stephen P. McCarthy, Laboratory Scale Composting Test Methods to Determine Polymer Biodegradability: Model Studies on Cellulose Acetate, *J Macromol. Sci.-Pure & Appl. Chem.*, V A32, No. 4, 613-628 (1995).

John E. Kemnitzer, Stephen P. McCarthy, Richard A. Gross, John Liggat, David J. Blundell and Mike Cox, "Crystallization Behavior of Predominantly -hydroxybutyrate)",βSyndiotactic Poly ( *J. Environ. Polym. Deg.* vol. 3(1), 37-47 (1995).

Gregory A. Birrer, Anne-Marie Cromwick and Richard A. Gross, □-Poly(glutamic acid) formation by *Bacillus licheniformis* ATCC 9945A: Physiology and Biochemical Studies, *Int. J. Biol. Macromol.* ; 16(5) 265-275 (1994).

Ji-Dong Gu, Shunjuan Yang, Robert Welton, David Eberiel, Stephen P. McCarthy and Richard A. Gross, "Effect of Environmental Parameters on the Degradability of Polymer Films in Laboratory Scale Composting Reactors", *J. Environ. Polym. Deg.*, vol. 2, No. 2, 129-135 (1994).

Deeleep K. Rout, Shikha P. Barman, Satish K. Pulapura, and Richard A. Gross, Cholesteric Mesophases Formed by the Modified Biological Macromolecule 3,6-O-(Buyl Carbamate)-N-phthaloyl Chitosan, *Macromolecules*, vol. 27, 2945-2950 (1994).

Michael S. Reeve, Stephen P. McCarthy, Milton J. Downey and Richard A. Gross, Polylactide Stereochemistry: Effect on Enzymatic Degradability, *Macromolecules*, vol. 27, 825-831 (1994).

Richard A. Gross, "Bacterial Polyesters: Structural Variability in Microbial Synthesis", in *Biomedical Polymers: Designed-to-Degrade Systems*, Ed. S. Shalaby, Hanser Publishers, NY, pp. 2-9 (1994).

Herbert W. Ulmer, Richard A. Gross, Mario Posada, Paul Weisbach, R. Clinton -hydroxyalkanoates)βFuller and Robert W. Lenz, Bacterial Production of Poly( Containing Unsaturated Repeating Units by Rhodospirillum rubrum, *Macromolecules*, vol. 27, 1675-1679 (1994).

Ji-Dong Gu, David Eberial, Stephen P. McCarthy and Richard A. Gross, "Degradation and Mineralization of Cellulose Acetate in Simulated Thermophilic Compost Environments", *J. Environ. Polym. Deg.*, vol. 1, No. 4, 281-291 (1993).

Ji-Dong Gu, Sarah Coulter, David Eberiel, Stephen P. McCarthy and Richard A. Gross, "A Respirometric Method to Measure Mineralization of Polymeric Materials in a Matured Compost Environment", *J. Environ. Polym. Deg.*, vol. 1, No. 4, 293-299 (1993).

Richard A. Gross, Gregory A. Birrer, Anne-Marie Cromwick, Stephen A. Giannos and Stephen P. McCarthy, "Polymers From Biotechnology: Bacterial Polyesters and -Poly(glutamic Acid)", inγ *Biotechnological Polymers: Medical, Pharmaceutical and Industrial Applications*, Ed. C. G. Gebelin, Technomic Publishing Co., PA, pp. 200-213 (1993).

Deeleep K. Rout, Satish K. Pulapura and Richard A. Gross, "Gel-Sol Transition and Thermotropic Behavior of a Chitosan Derivative in Lyotropic Solution", *Macromolecules*, vol. 26., 6007-6010 (1993).

Deeleep K. Rout, Satish K. Pulapura and Richard A. Gross, "Liquid Crystalline Characteristics of Site-Selectively-Modified Chitosan", *Macromolecules*, vol. 26, 5999-6006 (1993).

John E. Kemnitzer, Stephen P. McCarthy, and Richard A. Gross, "Syndiospecific -Butyrolactone to Form PredominantlyβRing-Opening Polymerization of -hydroxybutyrate) Using Tin (IV) Catalysts",βSyndiotactic Poly(*Macromolecules*, vol. 26, 6143-6150 (1993).

John E. Kemnitzer, Stephen P. McCarthy, and Richard A. Gross, "The -hydroxybutyrate) by theβPreparation of Predominantly Syndiotactic Poly( Tributyl Methoxide Catalyzed Ring-Opening Polymerization of Racemic -Butyrolactone"β *Macromolecules*, vol. 26, pp. 1221-1229 (1993).

Michael S. Reeve, Stephen P. McCarthy and Richard A. Gross, "The Preparation and -Caprolactone) ande-hydroxybutyrate)-Poly(βCharacterization of [R]-Poly( -hydroxybutyrate)-Poly(lactide) Degradable Diblock Copolymers",β[R]-Poly( *Macromolecules*, vol. 26, pp. 888-894 (1993).

Ji-Dong Gu, David. T. Eberiel, Stephen. P. McCarthy and Richard. A. Gross, "Cellulose Acetate Biodegradability Upon Exposure To Simulated Aerobic Composting And Anaerobic Bioreactor Environments", *J Environ. Polym. Degrad.*, 1(2), (1993).

Co-pending U.S. Appl. No. 11/579,833, filed Nov. 7, 2006.
Co-pending U.S. Appl. No. 11/596,012, filed Nov. 9, 2006.
Co-pending U.S. Appl. No. 11/632,638, filed Jan. 16, 2007.
Co-pending U.S. Appl. No. 11/658,154, filed Feb. 13, 2007.
Co-pending U.S. Appl. No. 11/663,338, filed Mar. 21, 2007.
Co-pending U.S. Appl. No. 11/663,342, filed Mar. 21, 2007.
Co-pending U.S. Appl. No. 11/792,723, filed Jun. 11, 2007.

International Search Report of PCT/US05/25308, mailed Jul. 21, 2006.

International Preliminary Report on Patentability; International Application No. PCT/US2005/026000 (6 pgs), International Filing date Jul. 22, 2005.

Nakamura, S., et al; "Protective effect of D-beta-hydroxybutyrate on corneal epithelia in dry eye conditions through suppression of apoptosis"; IVOS, vol. 44, No. 11, Nov. 2003, pp. 4682-4688, XP009051914.

Koustova, E., et al; "Ketone and pyruvate Ringer's solutions decrease pulmonary apoptosis in a rat model of severe hemorrhagic shock and resuscitation", Surgery (St. Louis), vol. 134, No. 2, Aug. 2003; pp. 267-274, SP002339609 (Abstract).

Zou, Zhitian, et al; "dl-3-Hydroxybutyrate administration prevents myocardial damage after coronary occlusion in rat hearts"; American Journal of Physiology, vol. 283, No. 5, Part 2, Nov. 2002, pp. H1968-H1974, XP009051908 (Abstract).

Ducouedic, H., et al; "Contribution to the Study of Sodium 4-Hydroxybutyrate (4HO) in the Treatment of Acute Anxiety States"; *Agressologie: Revue International De Physio-Biologie et de Pharmacologie Appliquees Aux Effects De L'Agression*; vol. 27, pp. 73-86; Jan.-Feb. 1964; XP008055966.

Song, Cai, et al; "Effects of dietary n-3 or n-6 fatty acids on interleukin-1beta-induced anxiety, stress, and inflammatory responses in rats"; *Journal of Lipid Research*; vol. 44, No. 10; pp. 1984-1991; Oct. 2003; XP008055958.

Wright, J.; "Treatment of chronic anxiety and associated physical complaints with niacinamide and essential fatty acids: Two cases"; *Journal of Orthomolecular Medicine 1992 Canada*; vol. 7, No. 3; pp. 182-186; XP008055961.

Gottschalk, L.A., et al; "Anxiety and plasma free fatty acids (FFA)"; *Life Sciences*; vol. 8, No. 2, Jan. 15, 1969; pp. 61-68; XP008055955.

Suzuki, S., et al; "Daily omega-3 fatty acid intake and depression in Japanese patients with newly diagnosed lung cancer"; *British Journal of Cancer*; vol. 90, No. 4; pp. 787-793; Feb. 23, 2004; XP008055956.

Hakkarainen, R., et al; "Food and nutrient intake in relation to mental wellbeing"; *Nutritional Journal 'Electronic Resource'*; vol. 3; p. 14; Sep. 13, 2004; XP008055959.

Ahrens, H., et al; (1974), "Mehrdimensionale Varianzanalyse"; *Akademie-Verlag*, Berlin.

Dimpfel, W., et al; (1986), "Radioelectroencephalography (Tele-Stereo-EEG) in the Rat as a Pharmacological Model to Differentiate the Central Action of Flupirtine from That of Opiates, Diazepam and Phenobarbital"; *Neurophychobiology* 16: 163-168.

Dimpfel, W., et al; (1987), "Radioelectroencephalographic Comparison of Memantine with Receptor-Specific Druigs Acting on Dopaminergic Transmission in Freely Moving Rats"; *Neuropsychobiology* 18: 212-218.

Dimpfel, W., et al; (1988), Monitoring of the effects of antidepressant drugs in the freely moving rat by radioelectroencephalography (Tele-Stereo-EEG); *Neurobiology* 19: 116-120.

Dimpfel, W., et al; (1992), "Different neuroleptics show common dose and time dependent effects in quantitative field potential analysis in freely moving rats"; *Psychopharmacology* 107: 195-202.

Dimpfel, W., et al; (2001), Norepinephrine, EEG theta waves and sedation; *Brain Pharmacology* 1: 89-97.

Dimpfel, W.; (2003), Preclinical Data Base of Pharmaco-Specific Rat EEG Fingerprints (Tele-Stereo-EEG); *European Journal of Medical Research* 8: 199-207.

Paxinos G., et al; (1982), The rat brain in stereotactic coordinates, *Academic Press*, New York.

Suzuki, M., et al; (2001), "Effect of β-Hydroxybutyrate, a Cerebral Function Improving Agent, on Cerebral Hypoxia, Anoxia and Ischemia in Mice and Rats"; Jpn. J. Pharmacol. 87, 143-150.

Suzuki, M., et al; (2002), "β-Hydroxybutyrate, a Cerebral Function Improving Agent, Protects Rat Brain Against Ischemic Damage Caused by Permanent and Transient Focal Cerebral Ischemia"; Jpn. J. Pharmacol. 89, 36-43.

"Biopolymers and -oligomers of (R)-3-Hydroxyalkanoic Acids—Contributions of synthetic Organic Chemists": D Seebach et al: Ernst Schering Research Foundation; 1995.

"Biodegradation of cyclic and substituted linear oligomers of poly(3-hydroxybutyrate)": Helmut Brandl et al: Can. J. Microbiol 41(Suppl. 1); 1995; pp. 180-186.

"Direct degradation of the biopolymer poly[(R)-3-hydroxybutyric acid] to (R)-3-hydroxybutanoic acid and its methyl ester"; D Seebach et al; Org. Synth. 71; 1992; pp. 39-47.

"Cyclische Oligomere von (R)-3-Hydroxybuttersaure: Herstellung und strukturelle Aspekte"; von Dietmar et al: Helvetica Chimica Aeta: vol. 76; 1993; pp. 2004-2016.

"Poly(hydroxyalkanoates): A Fifth Class of Physiologically Important Organic Biopolymers?"; Hans-Martin Muller et al; Angew. Chem.; 1993.

"Intractable epilepsy"; Avinoam Scuper et al; The Lancet, vol. 353; Apr. 10, 1999; p. 1238.

"Energy Metabolism and the Regulation of Metabolic Processes in Mitochondria"; R.L. Veech et al; Academic Press; 1972; pp. 170-183.

"Nontoxic Amyloid β Peptide$_{1-42}$ suppresses Acetylcholine synthesis"; Minako Hoshi et al; The Journal of Biological Chemistry; vol. 272, No. 4; Jan. 1997; pp. 2038-2041.

"Alternate Fuel Utilization by Brain"; George F. Cahill Jr. et al; Cereral Metabolism and Neural Function; Williams Wilkins, London; pp. 234-242.

"Preparation and Structure of Oligolides from (R)-3-Hydroxypentanoic Acid and comparison with the Hydroxybutanoic-Acid Derivatives: A Small Change with Large Consequences"; Dieter Seebach et al; Helvetica Chimica Acta—vol. 77; 1994; pp. 2007-2033.

"The Triolide of (R)-3-Hydroxybutyric acid—Direct Preparaton from Polyhydroxybutyrate and Formation of a Crown Estercarbonyl Complex with Na Ions"; Dieter Seebach et al; Angew. Chem. Int.; 1992; pp. 434-435.

"Ketone bodies as substrates"; A.J. Rich; Proceedings of the Nutrition Society, vol. 49; 1990; pp. 361-373.

"The Dimer and Trimer of 3-Hydroxybutyrate Oligomer as a Precursor of Ketone Bodies for Nutritional Care"; Osamu Tasaki et al; Journal of Parenteral and Enteral Nutrition, vol. 23, No. 6; 1999; pp. 321-325.

"Effect of 3-hydroxybutyrate in obese subjects on very-low-energy diets and during therapeutic starvation"; G.L.S. Pawan et al; The Lancet; Jan. 1983; pp. 15-17.

"The untoward effects of the anoins of dialysis fluids"; R.L. Veech et al; Kidney internation, vol. 34; 1988; pp. 587-597.

"Transport of poly-β-hydroxybutyrate in human plasma"; Rosetta N. Reusch et al; Biochimica et Biophysica Aeta 1123; 1992; pp. 33-40.

"Human xenobiotic metabolizing esterases in liver and blood"; N.W. McCracken et al; Biochemical Pharmacology vol. 46, No. 7: 1993; pp. 1125-1129.

"Detection, synthesis, structure, and function of oligo(3-hydroxyalkanoates): contributions by synthetic organic chemists"; Dieter Seebach et al: International Journal of Biological Macromolecules 25; 1999; pp. 217-236.

"The toxic impact of parenteral solutions on the metabolism of cells: a hypothesis for physiological parenteral therapy"; R.L. Veech et al; The Americal Journal of Clinical Nutrition 44; Oct. 1986; pp. 519-551.

"Association between features of the insulin resistance syndrome and Alzheimer's disease independently of apolipoprotein E4 phenotype: cross sectional population based study"; Johanna Kuusisto et al; BMJ vol. 315; Oct. 25, 1997; pp. 1045-1049.

"Novel calcium ion channel is a pore without protein"; Karen Hopkin; The Journal of NIH Research vol. 9; Nov. 1997; pp. 25-26.

"Physiological Roles of Ketone Bodies as Substrates and Signals in Mammalian Tissues"; Alison M. Robinson et al; Physiological Reviews; vol. 60, No. 1; Jan. 1980; pp. 143-153.

"Proof for a nonproteinaceous calcium-selective channel in Escherichia coli by total synthesis from (R)-3-hydroxybutanoic acid and inorganic polyphosphate"; Sudipto Das et al; Proc. Natl. Acad. Sci. USA; vol. 94; Aug. 1997; pp. 9075-9079.

"New Clues to Alzheimer's disease: Unraveling the roles of amyloid and tau"; Bruce A. Yankner; Nature Medicine vol. 2, No. 8; Aug. 1996; pp. 850-852.

"An intracellular protein that binds amyloid-β peptide and mediates neurotoxicity in Alzheimer's disease"; Shi Du Yan et al; Nature, vol. 389; Oct. 16, 1997; pp. 689-695.

"Alternate Fuel Utilization by Brain"; George F. Cahill, Jr. et al; Cerebral Metabolism and Neural Function; Williams & Wilkins; Chapter 26, pp. 234-242.

"Blood-Brain Barrier Transport of Metabolic Substrates"; William H. Oldendorf; Cerebral Metabolism and Neural Function; Williams & Wilkins; Chapter 15, pp. 127-132.

"β-hydroxybutyrate suppresses pentylenetetrazol (PTZ)—induced seizures in young adult rats"; Sarah Lustig et al; Epilepsia, vol. 39, Suppl. 6; 1998; 2.020; p. 36.

"β-hydroxybutyrate potentiates $gaba_A$-mediated inhibitory postsynaptic potentials in immature hippocampal CA1 neurons"; Shundi Ge et al; Epilepsia, vol. 38, Suppl. 6; 1998; E.06; p. 135.

"The effect of ketone bodies, β-hydroxybutyrate, and acetoacetate on acute seizure activity in hippocampal CA1 neurons"; Charles E. Niesen et al; Epilepsia, vol. 39, Suppl. 6; 1998; 2.015; Pae 35.

"Biologica-Chemical preparation of 3-hydroxycarboxylic acids and their use in EPC-synthesis"; Dieter Seebach et al: Laboratorium fur Organisch Chemie der Eidenossischen Technischen Hochschule; pp. 85-126.

"Dietary Nonprotein calories and cerebral infarction size in rats"; Claudia Robisnon et al; Stroke, vol. 23, No. 4; Apr. 1992; pp. 564-568.

"Hypoxia and β-hydroxybutyrate acutely reduce glucose extraction by the brain in anesthetized dogs"; Albert S. Y. Change et al; Can J Poyiol Pharmacol, vol. 71; 1993; pp. 465-472.

"γ-Hydroxybutyrate: Cerebral metabolic, Vascular, and Protective effects"; Alan A. Artru et al; J Neurochem. vol. 35, No. 5; 1980; pp. 1114-1119.

"Effect of sodium hydroxybutyrate on the cerebral circulation and regional vasomotor reflexes"; E.A. Bendikov et al; Plenum Publishing Corporation; 1980; pp. 1287-1292.

"Oxidative metabolism deficiencies in brains of patients with Alzheimer's disease"; S. Hoyer; Acta Neurol Scand, Suppl. 165; 1996; pp. 18-24.

"The ins and outs of amyloid-β"; Konrad Beyreuther et al; Nature, vol. 389; Oct. 16, 1997; pp. 677-678.

"Metabolism of (R,S)-1,3-butanediol acetoacetate esters, potential parenteral and enteral nutrients in conscious pigs"; Sylvain Desrochers et al; The American Physiological Society; 1995; pp. 660-667.

"The Gibbs-Donnan Near-equilibrium System of Heart"; Takashi Masuda et al; The Journal of Biological Chemistry, vol. 265, No. 33; Nov. 25, 1990; pp. 20321-20344.

"Nutritional and metabolic studies in humans with 1,3-butanediol"; Richard B. Tobin et al; Federation Proceedings vol. 34, No. 12; Nov. 1975; pp. 2171-2176.

"Utilization of 1,3-Butanediol and Nonspecific Nitrogen in Human Adults"; Constance Kies et al; Nebraska Agriculture Research Station Journal No. 3489; pp. 1115-1163.

"Alzheimer's Disease: Genotypes, Phenotype, and Treatments"; Dennis J. Selkoe; Science, vol. 275; Jan. 31, 1997; pp. 630-631.

"The β/α Peak Height Ratio of ATP"; Kieran Clarke et al; The Journal of Biological Chemistry, vol. 271, No. 35, Aug. 30, 1996; pp. 21142-21150.

"Control of Glucose Utilization in Working Perfused Rat Heart"; Yoshishiro Kashiwaya et al; The Journal of Biological Chemistry, vol. 269, No. 41; Oct. 14, 1994; pp. 25502-25514.

"Regulation of mitochondrial pyruvate dehydrogenase activity by tau protein kinase I/glycogen synthase kinase 3β in brain"; Minako Hoshi et al; Proc Natl. Acad. Sci. USA, vol. 93; Apr. 1996; pp. 2719-2723.

Stress and Glucocorticoid; Rachel Yehuda; Science, vol. 275; Mar. 14, 1997; pp. 1662-1663.

"Nontoxic Amyloid β Peptide$_{1-42}$ Suppresses acetylcholine synthesis"; Minako Hoshi et al; The Journal of Biological Chemistry, vol. 272, No. 4; Jan. 24, 1997; pp. 2038-2041.

"Metabolic engineering and human disease"; Martin L. Yarmush et al; Nature Biotechnology, vol. 15; Jun. 15, 1997; pp. 525-528.

"Metabolism of R- and S-1,3-butanediol in perfused livers from meal-fed and starved rats"; Sylvain Desrochers et al; Biochem. J. vol. 285; 1992; pp. 647-653.

"Metabolism of 2,3-Butanediol Stereoisomers in the Perfused Rat Liver"; Jane A. Montgomery et al; The Journal of Biological Chemistry, vol. 268, No. 27; 1993; pp. 20185-20190.

"Nutritional and metabolic studies in humans with 1,3-butanediol"; Richard B. Tobin et al; Federation Proceedings vol. 34, No. 12; Nov. 1975; pp. 2171-2176.

"Metabolic effects of a D-β-hydroxybutyrate infusion in septic patients: Inhibition of lipolysis and glucose production but not leucine oxidations"; Michel Beylot et al; Critical Care Medicine, vol. 22, No. 7; Jul. 1994; pp. 1091-1098.

"Hyperinsulinaemia and Alzheimer's Disease"; George Razay et al; Age and Ageing; 1994; pp. 398-399.

"Peripheral glucose metabolism and insulin sensitivity in Alzheimer's disease"; Kilander et al; Acta Neurol Scand; 1993; pp. 294-298.

"Effect of Sodium Hydroxybutyrate of the cerebral circulation and regional vasomotor reflexes"; Bendikov et al; Byulleten 'Eksperimental'noi Biologii i Meditsiny, vol. 88; No. 11; Nov. 1979; pp. 555-557.

"Tau protein Mutations confirmed as neuron killers"; Gretchen Vogel; Science, vol. 280; Jun. 5, 1998; pp. 1524-1525.

"Diagnosing dementia with Lewy bodies"; Ian G. McKeith et al; The Lancet, vol. 354; Oct. 9, 1999; pp. 1227-1228.

"R,S-1,3-butanediol acetoacetate esters, potential alternates to lipid emulsions for total parenteral nutrition"; Sylvain Desrochers et al; Nutritional Biochemistry vol. 6; 1995; pp. 111-118.

"Substrate signaling by insulin: a ketone bodies ratio mimics insulin action in heart"; Yoshihiro Kashiwaya e ta; The American Journal of Carliology, vol. 80 (3A); Aug. 4, 1997; pp. 50-64.

"Insulin, ketone bodies, and mitochondrial energy transduction"; Kiyotaka Sato et al; The FASEB Journal, vol. 9; May 1995; pp. 651-658.

"Regulation of GABA Level in Rat Brain Synaptosomes: Fluxes through enzymes of the GABA shunt and effects of glutamate, calcium, and ketone bodies"; Maria Erecinska et al; Journal of Neurochemistry, vol. 67, No. 6; 1996; pp. 2325-2334.

"The Metabolism of Acetone in Rat"; Joseph P. Cassazza et al; The Journal of Biological Chemistry, vol. 259, No. 1; Jan. 10, 1984; pp. 231-236.

Jiang, Z. Z.; Liu, C.; Xie, W. C.; Gross, R. A., Controlled lipase-catalyzed synthesis of poly(hexamethylene carbonate). *Macromolecules*, 40 (22), 7934-7943 (2007).

Shah, V.; Baldrian, P.; Eichlerova, I.; Dave, R.; Madamwar, D.; Nerud, F.; Gross, R. Influence of dimethyl sulfoxide on extracellular enzyme production by *Pleurotus ostreatus*. *Biotechnology Letters* 28 (9): 651-655 (2006).

Hu, J; Gao, W.; Kulshrestha, A.; Gross, R.A. "Sweet polyesters": Lipase-catalyzed condensation—Polymerizations of alditols, *Macromolecules* 39 (20): 6789-6792 (2006).

Azim, A; Shah, V.; Doncel, G.F.; Peterson, N.; Gao, W.; Gross, R. Amino acid conjugated sophorolipids: A new family of biologically active functionalized glycolipids. *Bioconjugate Chemistry* 17 (6): 1523-1529 (2006).

Azim, H.; Dekhterman, A.; Jiang, Z.Z.; Gross, R.A. *Candida antarctica* lipase B-catalyzed synthesis of poly(butylene succinate): Shorter chain building blocks also work, *BioMacromolecules* 7 (11): 3093-3097 (2006).

Shah V, Doncel GF, Seyoum T, Eaton KM, Zalenskaya I, Hagver R, Azim A, Gross R. Sophorolipids, microbial glycolipids with anti-human immunodeficiency virus and sperm-immobilizing activities. *Antimicrob Agents Chemother*; 149; 1-8 (2005).

Mijovic, J.; Bian, Y.; Gross, R. A.; Chen, B. Dynamics of Proteins in Hydrated State and in Solution As Studied by Dielectric Relaxation Spectroscopy *Macromolecules*; 38(26) 10812-10819 (2005).

Chakraborty. S,Sahoo. B,Teraoka, Gross.RA Solution properties of starch nanoparticles in water and DMSO as studied by dynamic light scattering *Carbohydrates polymers*; 60(4); 475-481, (2005).

Nakaoki, T.; Mei, Y.; Miller, L.-M.; Kumar, A; Kalra, B; Miller, E.-M.; Kirk, O.; Christensen, M.; Gross, R.A. "Candida antartica Lipase B catalyzed polymerization of lactones: Effects of immobilization matrices on polymerization kinetics and Molecular Weight" *Industrial Biotechnology*; 1(2) 126-134 (2005).

Sahoo, B.; Brandstadt, K. F.; Lane, T. H.; Gross, R. A. "Sweet Silicones": Biocatalytic Reactions to Form Organosilicon Carbohydrate Macromers *Org. Lett.*; 7(18); 3857-3860 (2005).

Loos, K.; Kennedy, S. B.; Eidelman, N.; Tai, Y.; Zharnikov, M.; Amis, E. J.; Ulman, A.; Gross, R. A. Combinatorial Approach To Study Enzyme/Surface Interactions *Langmuir*; 21(12); 5237-5241 (2005).

Kulshrestha, A. S.; Sahoo, B., Gao, W.; Fu, H. and Gross, R.A. "Lipase Catalysis. A Direct Route to Linear Aliphatic Copolyesters of Bis(hydroxymethyl)butyric Acid with Pendant Carboxylic Acid Groups", *Macromolecules*; 38(8); 3205-3213 (2005).

Kulshrestha, A. S.; Gao, W.; Gross, R.A. "Glycerol Copolyesters: Control of Branching and Molecular Weight Using a Lipase Catalyst", *Macromolecules*, (2005); 38(8); 3193-3204.

Ceccorulli, G.; Scandola, M.; Kumar, A.; Kalra, B.; Gross, R. A., "Cocrystallization of Random Copolymers of—Pentadecalactone and -Caprolactone Synthesized by Lipase Catalysis" *BioMacromolecules*; 6(2); 902-907 (2005).

Chakraborty, S.; Sahoo, B.; Teraoka, I.; Miller, L. M.; Gross, R.A. "Enzyme-Catalyzed Regioselective Modification of Starch Nanoparticles" *Macromolecules*; 38(1); 61-68 (2005).

Zhang, L., Somasundaran, P., Singh, S. K., Felse, A. P., Gross, R.A. Synthesis and interfacial properties of sophorolipid derivatives *Colloids and Surfaces A: Physicochem.Eng. Aspects*; 240; 75-82 (2004).

Zhou, S., Xu, Chang.., Wang, J., Gao, W., Akhverdiyeva., Shah, V., Gross, R. A. Supramolecular Assembles of a Naturally Derived Sopholipid. *Langmuir*; 20; 7926-7932 (2004).

Kalra, B.; Kumar, A.; Gross, R. A.; Baiardo, M.; Scandola, M. "Chemoenzymatic Synthesis of New Brush Copolymers Comprising Poly( -pentadecalactone) with Unusual Thermal and Crystalline Properties" *Macromolecules*; 37(4); 1243-1250 (2004).

Mahapatro, A.; Kumar, A.; Kalra, B.; Gross, R. A. "Solvent-Free Adipic Acid/1,8-Octanediol Condensation Polymerizations Catalyzed by *Candida antartica* Lipase B" *Macromolecules*; 37(1); 35-40 (2004).

Van As, B. A. C.; Thomassen, P.; Kalra, B.; Gross, R. A.; Meijer, E. W.; Palmans, A. R. A.; Heise, A. "One-Pot Chemoenzymatic Cascade Polymerization under Kinetic Resolution Conditions" *Macromolecules*; 37(24); 8973-8977 (2004).

Mahapatro, A.; Kumar, A.; Gross, R. A.; "Mild, Solvent-Free -Hydroxy Acid Polycondensations Catalyzed by *Candida antarctica* Lipase B." *BioMacromolecules*; 5(1); 62-68 (2004).

Loeker, F. C.; Duxbury, C. J.; Kumar, R.; Gao, W.; Gross, R. A.; Howdle, S. M. Enzyme-Catalyzed Ring-Opening Polymerization of -Caprolactone in Supercritical Carbon Dioxide. *Macromolecules*; 37(7); 2450-2453 (2004).

Hyung-Pil, S, Chung, C.H., Kim, S.K., Gross, R.A., Kaplan., D.L. Lee, J.W. Mass Production of Pullulan with Optimized Concentrations of Carbon and Nitrogen sources by *Aureobasidium pullulans* HP-2001 in a 100-L Bioreactor J. Microbol. Biotechnol.; 14,(2), 237-242 (2004).

Mei, Y., Kumar, A, Gao, W, Gross, R.A., Kennedy, S.B., Washburn, N.R., Amis, E.,J., Elliot, John T. Biocompatibility of sorbitol-containing polyesters. Part 1: Synthesis, surface analysis and cell response in vitro; *Biomaterials*; 25; 4195-4201 (2004).

Singh, S,K, Felse, A. P., Nunez, A., Foglia, T.A. and Gross, R.A. Regioselective Enzyme-Catalyzed Synthesis of Sophorolipid Esters, Amides and Multifunctional Monomers. *J. Org. Chem.*; 68; 5466-5477 (2003).

Kumar, A.; Kulshrestha, A. S.; Gao, W.; Gross, R. A.; Versatile Route to Polyol Polyesters by Lipase Catalysis *Macromolecules*; 36(22); 8219-8221 (2003).

Mei, Y.; Miller, L.; Gao, W.; Gross, R. A.; Imaging the Distribution and Secondary Structure of Immobilized Enzymes Using Infrared Microspectroscopy *BioMacromolecules*; 4(1); 70-74 (2003).

Mahapatro, A.; Kalra, B.; Kumar, A.; Gross, R. A.; Lipase-Catalyzed Polycondensations: Effect of Substrates and Solvent on Chain Formation, Dispersity, and End-Group Structure *BioMacromolecules*; 4(3); 544-551 (2003).

Fu, H.; Kulshrestha, A. S.; Gao, W.; Gross, R. A.; Baiardo, M.; Scandola, M., Physical Characterization of Sorbitol or Glycerol Containing Aliphatic Copolyesters Synthesized by Lipase-Catalyzed Polymerization *Macromolecules*; 36(26); 9804-9808 (2003).

Dyal, A., Loos, Katja., Noto, M., Chang, S.W., Spagnoli, C., Shafi, Kurikka V.P.M., Ulman, A., Cowman,M.,Gross. R.A. Activity of *Candida rugosa* Lipase -Fe2O3 Magnetic Nanoparticlesγ Immobilized on *J. Am. Chem. Soc.*; 125; 1684-1685 (2003).

Mei, Y, Kumar, A, Gross; R.A., "Kinetics and Mechanism of *Candida antarctica* Lipase B Catalyzed Solution Polymerization of -Caprolactone", *Macromolecules*; 36(15); 5530-5536 (2003).

Gross, R. A., Kalra, B; "Biodegradable Polymers for the Environment", *Science*, 297, 803-806 (2002).

Focarete, M. L.; Gazzano, M.; Scandola, M.; Kumar, A.; Gross, R. A.; -Pentadecalactone and Trimethylene Carbonate from Lipaseω"Copolymers of Catalysis: Influence of Microstructure on Solid-State Properties", *Macromolecules*; 35(21); 8066-8071, (2002).

Kumar, A.; Gross, R. A.; Wang, Y.; Hillmyer, M. A.; "Recognition by Lipases -Hydroxyl Macroinitiators for Diblock Copolymer Synthesis"ωof *Macromolecules*; 35(20); 7606-7611, (2002).

Kumar, R.; Gao, W.; Gross, R. A.; "Functionalized Polylactides: Preparation and Characterization of [L]-Lactide-co-Pentofuranose" *Macromolecules*; 2002; 35(18); 6835-6844.

Bankova, M.; Kumar, A.; Impallomeni, G.; Ballistreri, A.; Gross, R. A.; -caprolactone) Transesterificatione"Mass-Selective Lipase-Catalyzed Poly( Reactions", *Macromolecules*; 35(18); 6858-6866, (2002).

Hu, Shanghui; Gupta, Pankaj; Prasad, Ashok K.; Gross, Richard, A., Parmar, Virinder S. "Selective enzymatic epoxidation of dienes: Generation of Functional Enantiomerically Enriched Diene Monepoxy Monomers", *Tetrahedron Letters*; 43; 6763-6766 (2002).

B. Kalra and R.A. Gross, "HRP-Mediated Polymerizations of acrylamide and sodium acrylate", *Green Chemistry*; 4; 174-178 (2002).

Y. Mei, A. Kumar, and Richard A. Gross, "Probing Water-Temperature Relationships for Lipase-Catalyzed Lactone Ring-opening Polymerizations" *Macromolecules*; 35, 5444-5448 (2002).

R. Kumar and R.A. Gross, Biocatalytic Route to Well-Defined Macromers Built around a Sugar Core, *J. Am. Chem. Soc.*, 124(9): 1850-1851 (2002).

V Guilmanov, A Ballistreri, G Impallomeni, R.A. Gross, "Oxygen Transfer Rate and Sophorose Lipid Production by *Candida bombicola"*, *Biotechnol. and Bioeng*; 77(5), 489-494 (2002).

R. A. Gross, A Kumar, B Kalra, "In-vitro Enzyme Catalyzed Polymer Synthesis", *Chemical Reviews*, 101(7), 2097-2124 (2001).

J.W. Lee, F. Dang, W.G. Yeomans, A.L. Allen, R.A. Gross, D.L. Kaplan, Acetobacter xylinium ATCC 10245: Production of Chitosan-Cellulose and Chitin-Cellulose Exopolymers, *Applied and Environmental Microbiology*, 67(9), 3970-3975 (2001).

M. L. Focarete, A. Kumar, M. Scandola, R. A. Gross, "Physical Characterization of Poly(w-pentadecalactone) Synthesized by Lipase-Catalyzed Ring-Opening Polymerization", *J of Polymer Science, Part B: Polymer Physics*, 39(15), 1721-1729 (2001).

R.A.Gross, B.Kalra, A. Kumar "In-vitro Lipase Catalyzed Polyester and Polycarbonate Synthesis" *Applied Microbiology and Biotechnology*; 55(6), 655-660 (2001).

A Kumar, K Garg, R. A. Gross, "Lipase-Catalyzed Copolymerizations of Trimethylene Carbonate and w-Pentadecalactone" *Macromolecules*; 34; 3527-3533 (2001).

A Kumar, R.A Gross, "Lipase-Catalyzed Transesterification: New Synthetic Routes To Copolyesters", *J. Am. Chem. Soc.*; 122; 11767-11770 (2000).

A Kumar, B Kalra, A Dekhterman, R. A. Gross, "Efficient Ring-opening -Pentadecalactoneω-Caprolactone and εPolymerization and Co-polymerization of Catalyzed by *Candida antartica* Lipase B", *Macromolecules*, 33, 6303-6309 (2000).

K.S. Bisht, W Gao, R.A. Gross, "Glycolipids from *Candida bombicola*: Polymerization of 6-O-Acryl Sophorolipid Derivative", *Macromolecules*, 33, 6208-6210 (2000).

A. Kumar, R.A.Gross, J.D.Jenderoseck, "Poly(3-hydroxybutrate)-depolymerase from *Pseudomonas lemoignei*: catalysis of esterification in organic media" *Journal of Organic Chemistry*, 65, 7800-7806 (2000).

B Kalra, R.A. Gross, "HRP-Mediated Free Radical Polymerization of Methyl Methacrylate", *BioMacromolecules*, 1, 501-505 (2000).

A Kumar and R.A. Gross, *Candida antartica* Lipase B Catalyzed Polycaprolactone Synthesis: Effects of Organic Media and Temperature, *BioMacromolecules*, 1, 133-138 (2000).

J.W. Lee, W.G. Yeomans, A.L. Allen, F. Deng, R.A. Gross and D.L. Kaplan, "Biosynthesis of Novel Exopolymers by *Aureobasidium pullulans"*, *Appl. & Env. Microbiol.* 65(12), 5265-5271 (1999).

A. Gorkovenko, J. Zhang, R. A. Gross, D. L. Kaplan, A. L. Allen. Control of unsaturated fatty acid substituents in emulsans. *Carbohydrate Polymers*. 39,79-84 (1999).

R. D. Ashby, F.-Y. Shi and R.A. Gross, "A Tunable Switch to Regulate the Synthesis of Low and High Molecular Weight Microbial Polyesters" *Biotechnology and Bioengineering*, vol. 62 (1), (1999).

K. Bisht, R. Gross and D. Kaplan, "Enzyme-Mediated Regioselective Acylations of Sophorolipids", *J. Org. Chem.*, 64:3, 780-789 (1999).

X. Chen and R. Gross, "Versatile Copolymers from [L]-Lactide and [D]-Xylofuranose", *Macromolecules*, 32, 308-314 (1999).

K. S. Bissht, F. Deng, R. A. Gross, D. L. Kaplan and G. Swift, "Ethyl Glucoside as a Multifunctionl Initiator for Enzyme-Catalyzed regioselective Lactone Ring-opening Polymerization" *J. Am. Chem. Soc.*, vol. 120, 1363-1367 (1998).

K. S. Bisht, R. A. Gross and A. L. Cholli, "Enzymatic Polymerization of -CL) Containing an Ethyl Glucopyranoside Head Group: An NMR Study"εPoly( *Applied Spectroscopy*, 52 (11) 1472-1478, (1998).

Young Ko and Richard A. Gross -Poly(glutamic acid) Formation by Bacillusγ, "licheniformis ATCC 9945a: Physiological Effects of glucose and glycerol", *Biotechnol. and Bioeng.*, 57(40), 430-437 (1998).

D. L. Kaplan, J. Dordick, R. A. Gross, G. Swift. In Enzymes in Polymer Science, R. Gross, D. Kaplan, G. Swift, Editors; *American Chemical Society Symposium Series* 684: 2-17 (1998).

Kirpal S. Bisht, Lori A. Henderson, Yuri Y. Svirkin and Richard A. Gross, David L. Kaplan and Graham Swift, "Monomer and Polymer Synthesis by Lipase-Catalyzed Ring-Opening Reactions", In, *Enzymes in Polymer Synthesis*, Eds. R.A. Gross, D.L. Kaplan and G. Swift, ACS Symposium Series 684, ACS, Washington, 90-111 (1998).

Xianhai Chen, Stephen P. McCarthy and Richard A. Gross, Preparation and Characterization of Polycarbonates from 2,4,8,10-Tetraoxaspiro[5,5]undecane-3-one (DOXTC)-Trimethylenecarbonate (TMC) Ring-Opening Polymerizations, *J. Appl. Polym. Sci.*, vol. 67, 547-557 (1998).

Xianhai Chen, Stephen P. McCarthy and Richard A. Gross, "Synthesis, Characterization and Epoxidaion of an Aliphatic Polycarbonate from 2,2-[4,4-cyclohexene-1]-trimethylene tcarbonate (cHTC) Ring-Opening Polymerization", *Macromolecules*; 30, 3470-3476 (1997).

Fengying Shi, Richard D. Ashby and Richard A. Gross, "Formation by Alcaligenes species of Microbial Polyesters Containing 3-Hydroxybutyrate and 4-Hydroxybutyrate Repeat Units: Investigation of Product Homogeneity", *Macromolecules*, vol. 30, 2521-2523 (1997).

Richard Ashby, Feng-Ying Shi, and Richard A. Gross, "Use of poly(ethylene glycol) to control the end group structure and molecular weight of poly(3-hydroxybutyrate) formed by *Alcaligenes latus* DSM 1122," *Tetrahedron*, vol. 53, No. 45, 15209-115223 (1997).

Kirpal S. Bisht, Yuri Y. Svirkin, Lori A. Henderson, Richard A. Gross, David L. Kaplan and Graham Swift, Lipase-Catalyzed Ring-Opening Polymerization of Trimethylene Carbonate, *Macromolecules*, vol. 30, 7735-7742 (1997).

Jin W. Lee, Water G. Yeomans, Alfred L. Allen, David L. Kaplan, and Richard A. Gross, "Microbial production of water-soluble non curdlan type exopolymer-B with controlled composition by *Agrobacterium* sp. ATCC 31749" *Biotechnol. Letter.*, 19(12), 1217-1221 (1997).

Jin W. Lee, Water G. Yeomans, Alfred L. Allen, David L. Kaplan, and Richard A. Gross. "Production of zoogloea gum by *Zoogloea ramigera* with glucose analogs" *Biotechnol. Lett.* 19(8), 799-802 (1997).

Kirpal S. Bisht, Lori A. Henderson, Richard A. Gross, David L. Kaplan and Graham Swift, "Enzyme-Catalyzed Ring-Opening Polymerization of -pentadecalactone)",ωPoly( *Macromolecules*, vol. 30, 2705-2711 (1997).

Jin W. Lee, Water G. Yeomans, Alfred L. Allen, David L. Kaplan, Frank Deng, and Richard A. Gross. Exopolymers from curdlan production-incorporation of glucose-related sugars by *Agrobacerium* sp. ATCC 31749. *Can. J. Microbiol.* 43:149-156. (1997).

Jinwen Zhang, Alexander Gorkovenko, Richard A. Gross, Alfred L. Allen and David L. Kaplan Incorporation of 2-Hydroxyl Fatty Acids by *Acinetobacter calcoaceticus* RAG-1 to Tailor Emulsan Structure, *Intern. J. Biol. Macromol.*,vol. 20, 9-21 (1997).

Alexander Gorkovenko, Jinwen Zhang, Richard A. Gross, Alfred L. Allen and David L. Kaplan, "Bioengineering of Emulsifier Structure: Emulsan Analogs", *Can. J. Microbiol*, vol. 43, 384-390 (1997).

Renée T. Macdonald, Stephen P. McCarthy and Richard A. Gross, "Enzymatic Degradability of Poly(lactide): Effects of Chain Stereochemistry and Material Crystallinity", *Macromolecules*, vol. 29, 7356-7361 (1996).

Lori A. Henderson, Yuri, Y. Svirkin, Richard A. Gross, David L. Kaplan and -caprolactone: Effects ofεGraham Swift, "Enzyme Catalyzed Polymerizations of Initiator on Product Structure, Propagation Kinetics, and Mechanism", *Macromolecules*, vol. 29, 7759-7766 (1996).

David S. Roesser, Stephen P. McCarthy, Richard A. Gross and David L. Kaplan, "Effects of Substitution Site on Acetyl Amylose Biodegradability by Amylase Enzymes", *Macromolecules*, vol. 29, No. 1, 1-9 (1996).

Feng-Ying Shi, Richard Ashby and Richard A. Gross, "Use of Poly-(ethylene glycol)s to Regulate Poly(3-hydroxybutyrate) Molecular Weight during *Alcaligenes eutrophus* Cultivations", *Macromolecules*, vol. 29, 7753-7758 (1996).

Feng-Ying Shi, Denise Rutherford and Richard A. Gross, "Microbial Polyester Synthesis: Effects of Poly(ethylene glycol) on Product Composition, Repeat Unit Sequence and End Group Structure", *Macromolecules*, vol. 29, 10-17 (1996).

Richard A. Gross, Oh-young Kim, Denise R. Rutherford and Richard A. Newmark, "Cyanophenoxy-Containing Microbial Polyesters: Structural Analysis, Thermal Properties, Second Harmonic Generation and In-Vivo Biodegradability", *Polym. International*, vol. 39, 205-213 (1996).

Jin Xu, Stephen P. McCarthy and Richard A. Gross, "Racemic -propiolactone Polymerization by Organometallic Catalyst Systems", β-Methyl-α *Macromolecules*, vol. 29, No. 13, 4565-4571 (1996).

Anne-Marie Cromwick, Gregory A. Birrer and Richard A. Gross, "Effects of pH -Poly(glutamic acid) Formation by *Bacillus licheniformis* inγand Aeration on Controlled Batch Fermenter Cultures", *Biotechnol. Bioeng.*, vol. 50, 222-227 (1996).

Oh-young Kim, Richard A. Gross, W. James Hammar and Richard A. Newmark, -hydroxyalkanoates) Containing Fluorinatedβ"Microbial Synthesis of Poly( Side-Chain Substituents", *Macromolecules*, vol. 29, No. 13, 4572-4581 (1996).

Jin Xu, Richard A. Gross, David L. Kaplan and Graham Swift, "Chemoenzymatic -propiolactone) Stereocopolymers",β-methyl-αSynthesis and Study of Poly( *Macromolecules*, vol. 29, No. 13, 4582-4590 (1996).

Jin Xu, Richard A. Gross, David L. Kaplan and Graham Swift, "Chemoenzymatic Route to Poly(3-hydroxybutyrate)", *Macromolecules*, vol. 29, 3857-3861 (1996).

Jin Xu, Stephen P. McCarthy, Richard A. Gross and David L. Kaplan "Chitosan Film Acylation and Effects on Biodegradability", *Macromolecules*, vol. 29, 3436-3440 (1996).

Yuri Y. Svirkin, Jin Xu, Richard A. Gross, David L. Kaplan and Graham Swift, "Enzyme-Catalyzed Stereoselective Ring-Opening Polymerization of -propiolactone",β-Methyl-α *Macromolecules*, vol. 29, No. 13, 4591-4597 (1996).

Zbigniew Jedlinski, Marek Kowalczuk, Piotr Kurcok, Grazyna Adamus, Andrzej Matuszowicz, Wanda Sikorska, Richard A. Gross, Jin Xu, and Robert W. Lenz, -Butyrolactoneβ"Stereochemical Control in the Anionic Polymerization of Initiated with Alkali-Metal Alkoxides", *Macromolecules*, vol. 29, 3773-3777 (1996).

Oh-young Kim, Richard A. Gross and Denise R. Rutherford, "Bioengineering of -hydroxyalkanoates) for Advanced Material Applications: Incorporation ofβPoly( Cyano- and Nitrophenoxy Side Chain Substituents", *Can. J. Microbiol.*, vol. 41, supplement 1, 32-43 (1995).

Ferdinando F. Bruno, Joseph A. Akkara, Madhu Ayyagari, David L. Kaplan, Richard A. Gross, Graham Swift and Jonathan S. Dordick, "Enzymatic Modification of Insoluble Amylose in Organic Solvents", *Macromolecules*, vol 28, 8881-8883 (1995).

Renée T. Macdonald, Satish K. Pulapura, Yuri Y. Svirkin and Richard A. Gross, -Caprolactone Ring-Opening Polymerization",ε"Enzyme Catalyzed *Macromolecules*, 28, 73-78 (1995).

Anne-Marie Cromwick and Richard A. Gross, Effects of Manganese (II) on -Poly(glutamic acid)γ*Bacillus licheniformis* ATCC 9945A Physiology and Formation, *Int. J. Biol. Macromol.*, vol. 17, No. 5, 259-267 (1995).

Anne-Marie Cromwick and Richard A. Gross, Investigation by NMR of Metabolic -Poly(Glutamic Acid) Using 13C Labeled Citrate andγRoutes to Bacterial Glutamate as Media Carbon sources, *Can. J. Microbiol.*, vol. 41: 902-909 (1995).

Richard A. Gross, Ji-Dong Gu, David Eberiel and Stephen P. McCarthy, Laboratory Scale Composting Test Methods to Determine Polymer Biodegradability: Model Studies on Cellulose Acetate, *J Macromol. Sci.-Pure & Appl. Chem.*, V A32, No. 4, 613-628 (1995).

John E. Kemnitzer, Stephen P. McCarthy, Richard A. Gross, John Liggat, David J. Blundell and Mike Cox, "Crystallization Behavior of Predominantly -hydroxybutyrate)",βSyndiotactic Poly( *J. Environ. Polym. Deg.* vol. 3(1), 37-47 (1995).

Gregory A. Birrer, Anne-Marie Cromwick and Richard A. Gross, □-Poly(glutamic acid) Formation by *Bacillus licheniformis* ATCC 9945A: Physiology and Biochemical Studies, *Int. J. Biol. Macromol.* ; 16(5) 265-275 (1994).

Ji-Dong Gu, Shunjuan Yang, Robert Welton, David Eberiel, Stephen P. McCarthy and Richard A. Gross, "Effect of Environmental Parameters on the Degradability of Polymer Films in Laboratory Scale Composting Reactors", *J. Environ. Polym. Deg.*, vol. 2, No. 2, 129-135 (1994).

Deeleep K. Rout, Shikha P. Barman, Satish K. Pulapura, and Richard A. Gross, Cholesteric Mesophases Formed by the Modified Biological Macromolecule 3,6-O-(Buyl Carbamate)-N-phthaloyl Chitosan, *Macromolecules*, vol. 27, 2945-2950 (1994).

Michael S. Reeve, Stephen P. McCarthy, Milton J. Downey and Richard A. Gross, Polylactide Stereochemistry: Effect on Enzymatic Degradability, *Macromolecules*, vol. 27, 825-831 (1994).

Richard A. Gross, "Bacterial Polyesters: Structural Variability in Microbial Synthesis", in *Biomedical Polymers: Designed-to-Degrade Systems*, Ed. S. Shalaby, Hanser Publishers, NY, pp. 2-19 (1994).

Herbert W. Ulmer, Richard A. Gross, Mario Posada, Paul Weisbach, R. Clinton -hydroxyalkanoates)βFuller and Robert W. Lenz, Bacterial Production of Poly( Containing Unsaturated Repeating Units by *Rhodospirillum rubrum, Macromolecules*, vol. 27, 1675-1679 (1994).

Ji-Dong Gu, David Eberiel, Stephen P. McCarthy and Richard A. Gross, "Degradation and Mineralization of Cellulose Acetate in Simulated Thermophilic Compost Environments", *J. Environ. Polym. Deg.*, vol. 1, No. 4, 281-291 (1993).

Ji-Dong Gu, Sarah Coulter, David Eberiel, Stephen P. McCarthy and Richard A. Gross, "A Respirometric Method to Measure Mineralization of Polymeric Materials in a Matured Compost Environment", *J. Environ. Polym. Deg.*, vol. 1, No. 4, 293-299 (1993).

Richard A. Gross, Gregory A. Birrer, Anne-Marie Cromwick, Stephen A. Giannos and Stephen P. McCarthy, "Polymers From Biotechnology: Bacterial Polyesters and -Poly(glutamic Acid)", inγ

*Biotechnological Polymers: Medical, Pharmaceutical and Industrial Applications*, Ed. C. G. Gebelin, Technomic Publishing Co., PA, pp. 200-213 (1993).

Deeleep K. Rout, Satish K. Pulapura and Richard A. Gross, "Gel-Sol Transition and Thermotropic Behavior of a Chitosan Derivative in Lyotropic Solution", *Macromolecules*, vol. 26., 6007-6010 (1993).

Deeleep K. Rout, Satish K. Pulapura and Richard A. Gross, "Liquid Crystalline Characteristics of Site-Selectively-Modified Chitosan", *Macromolecules*, vol. 26, 5999-6006 (1993).

John E. Kemnitzer, Stephen P. McCarthy, and Richard A. Gross, "Syndiospecific β-Butyrolactone Ring-Opening Polymerization to Form Predominantly Syndiotactic Poly(β-hydroxybutyrate) Using Tin (IV) Catalysts", *Macromolecules*, vol. 26, 6143-6150 (1993).

John E. Kemnitzer, Stephen P. McCarthy, and Richard A. Gross, "Preparation of Predominantly Syndiotactic Poly(β-hydroxybutyrate) by the Tributyl Methoxide Catalyzed Ring-Opening Polymerization of Racemic β—Butyrolactone" *Macromolecules*, vol. 26, pp. 1221-1229 (1993).

Michael S. Reeve, Stephen P. McCarthy and Richard A. Gross, "The Preparation and Characterization of [R]-Poly(β-hydroxybutyrate)-Poly(ε-Caprolactone) and [R]-Poly(β-hydroxybutyrate)-Poly(lactide) Degradable Diblock Copolymers", *Macromolecules*, vol. 26, pp. 888-894 (1993).

Ji-Dong Gu, David. T. Eberiel, Stephen. P. McCarthy and Richard. A. Gross, "Cellulose Acetate Biodegradability Upon Exposure To Simulated Aerobic Composting And Anaerobic Bioreactor Environments", *J Environ. Polym. Degrad.*, 1(2), (1993).

* cited by examiner

OLIGOMERIC KETONE COMPOUNDS

This application is the U.S. National Phase of International Application PCT/US2005/025369, filed 19 Jul. 2005, which designated the U.S. PCT/GB2005/025369 claims priority to Provisional Application No. 60/588,990 filed 20 Jul. 2004. The entire content of these applications are incorporated herein by reference.

The present invention relates to novel oligomeric compounds which have utility as Nutraceutical and/or medicaments for producing ketosis in humans and animals for nutraceutical or therapeutic purposes.

It is known that ketone bodies, particularly (R)-3-hydroxybutyrate (D-β-hydrotybutyrate) and acetoacetate have both nutritional and therapeutic application in man and many animals. U.S. Pat. Nos. 6,136,862 and 6,232,345 (incorporated herein by reference) relate to the use of D-β-bydroxybutyrate, oligomers, esters and salts thereof, *inter alia,* in the treatment of cerebral edema and cerebral infarction. U.S. Pat. No. 6,207,856 and PCT/US 99/21015 also refer to β-hydroxybutyrate and its oligomers, esters and salts thereof in protecting against other forms of neurodegeneration *inter alia,* through their proposed ability to activate the TCA cycle and, through favorable redox reactions in cells and antioxidant activity, scavenge free radicals. β-hydroxybutyrate has also been demonstrated to have cardioprotectant effect and can increase cardiac efficiency (Sato et al, FASEB J, 9: 651-658, 1995).

U.S. Pat. Nos. 6,207,856, 6,136,862, 6,207,856 and PCT/US99/21015, incorporated herein by reference, teach that preferred ketogenic precursors for producing such ketosis are monohydric-, dihydric and trihydric alcoholic esters of (R)-3-hydroxybutyrate, but particularly a (R)-3-hydroxybutyryl ester of (R)-3-bydroxybutyrate, more preferably the diester formed from two molecules of (R)-3-hydroxybutyrate and one molecule of (R)-1, 3-butanediol.

However, it is also known that production of oligomers of (R)-3-hydroxybutyrate in pure form is problematic. PCT/US99/21015 exemplifies a ketogenic oligomer with a mixture of (R)-3-hydroxybutyrate trimer, tetramer and pentamer and exemplifies esters thereof with acetoacetyl trimer, tetramer and pentamer of (R)-3-hydroxybutyrate. Similarly, Hiraide et al (1999) *J Parenteral and Enteral Nutrition* Vol 23. No 6, discloses use of a mixture of dimer and trimer of (R)-3-hydroxybutyrate for studies on the ability of plasma to degrade these to the monomer.

In order to ensure a previously untested material is safe and appropriate for human administration by any route, it is necessary to evaluate all of its significant components for toxicity and efficacy In case of multicomponent materials it is thus necessary to test each one of these in a variety of toxicology and efficacy tests Such tasks can be extremely expensive and time consuming and inevitably is an important factor in any decision of whether or not to proceed with any particular assessment Furthermore, a mixture of different components may need to be produced in a set ratio for its safety and efficacy evaluation to be valid.

The present invention provides a single component oligomeric ketogenic material which is suitable for use in animals and man for therapeutic purposes.

In a first aspect of the present invention there is provided a compound of general formula $$R(OCH(CH_3)CH_2C(O))_n\text{—O-A}$$

wherein n is an integer of 3 to 10, A is the residue of a 3-keto alkan-1-ol and R is selected from the group consisting of H, $C_1$-$C_6$ alkyl and acetoacetyl Preferably A is the residue is of 4-hydroxy-2-butanone and the compound is a 4-hydroxy-2-butanone ester of an (R)-3-hydroxybutyrate oligomer having general formula

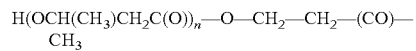

More preferably n is 3 to 5, still more preferably being 3.

In a second aspect of the present invention there is provided a nutraceutical or pharmaceutical composition comprising a compound of the first aspect together with a foodstuff or beverage component or a pharmaceutically acceptable carrier, diluent or excipient. Suitable foodstuff and beverage components may include, but are not limited to, edible oils, liquids, emulsions, gels and solids.

In a third aspect of the present invention there is provided the use of d compound of the first aspect of the present invention for the manufacture of a medicament for producing a physiologically acceptable ketosis. Such medicament will be suitable for treating, *inter alia*, diseases and medical conditions that are responsive to a bioavailable ketogenic agent, which include, but are not limited to, acute trauma, hemorrhagic shock, neurodegeneration, diabetes, and epilepsy, stroke, head trauma, myocardial infarction, congestive heart failure, pulmonary failure, kidney failure, obesity depression, pain and impaired cognition In a fourth aspect of the present invention there is provided a method for a the manufacture of a compound of the first aspect comprising reacting a cyclic oligomer of (R)-3-hydroxybutyrate containing between 3 and 10 (R)-3-hydroxybutyrate moieties with a 3-keto alkan-1-ol in an organic solvent in the presence of a lipase.

Preferably the solvent is a furan or pyran. The lipase may be selected from any commercially available lipase, but specifically may be selected from *Candida antarctica* lipasetype B (CAL-B or Novozym®435), *Pseudomonas cepecia* (PS; Anano Pharmaceuticals) and *Mucor miehei* lipase. Novozyme® 435 is available from Novozymes, Denmark.

Still more preferably the method is that wherein n is 3, A is a 4-hydoxy-2-butanone residue, R is H, the cyclic oligomer is (R)-3-hydroxybutyrate triolide, the alcohol is 4-hydroxy-2-butanone, the solvent is tetrahydrofuran (THF) and the lipase is, particularly that available from Novozyme as Novozyrn®435 (CAL-B).

By the term 'residue' as used in respect of A is intended the moiety remaining after the alcohol is esterified with the oligomer, ie. not including the alcoholic oxygen; thus the residue of 4-hydroxy-2-butanone is the group $CH_3$—(CO)—$CH_2$—CH2—, with the residue being connected to the rest of the molecule directly through its 4-carbon.

Compounds where R is $C_1$-$C_6$ alkyl and acetoacetyl can be made from the corresponding compound where R is H by simple esterification with the acetoacetate or an alkylating agent.

The present invention is advantageous over the copending application method using (R)-1,3-butanediol esters in so far as ketones such as butanone are: (i) miscible in non-polar organic media, (ii) has a small substituent in the β-position to the primary hydroxyl group, (iii) is equivalent to an oxidized fun of 1,3-butanediol, (iv) is achiral, (v) only yields one ester product thus simplifying purification and (vi) can use a number of known commercially available lipases.

Regarding starting materials for producing the compounds of the present invention, various cyclic esters of (R)-3-hydroxybutyrate are known in the art and are readily produced by known methods: see for example Seebach et al. Helvetia Chimica Acta Vol 71 (1988) pages 155-167, and Seebach et al. Helvetia Chimica Acta, Vol 77 (1994) pages 2007 to 2033 incorporated herein by reference.

The present invention will now be described further by reference to the following non-limiting Examples, Schemes and Figures. Further embodiments falling within the scope of the claim will occur to those skilled in the art in the light of these.

FIGURES

FIG. 1: The synthesis of (R,R,R)-4,8,12-trimethyl-1,5,9-trioxadodeca-2,6,10-trione [(R)-3-hydroxybutyrate triolide]

Figure 2:
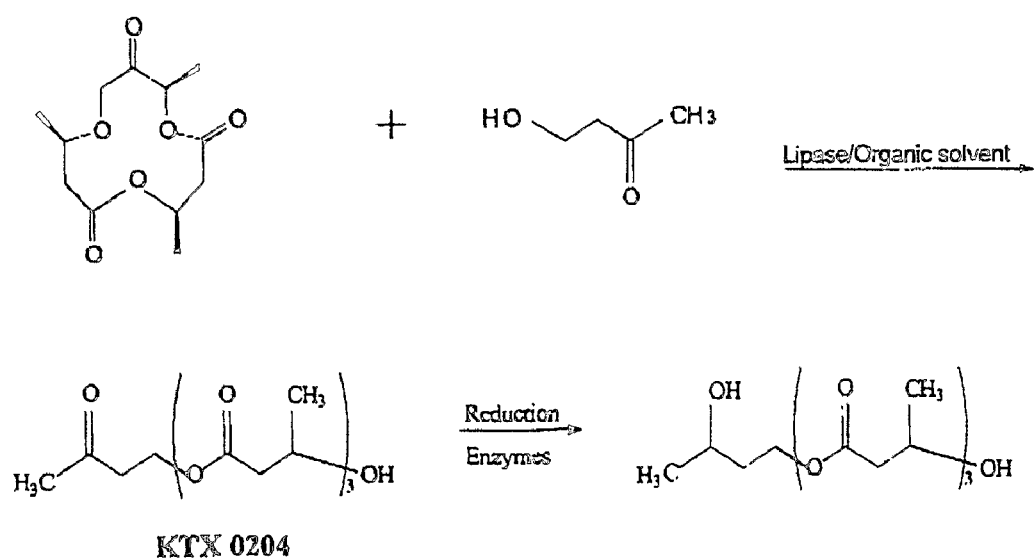

FIG. 2: The reaction scheme for synthesis of a 2-ketobutan-4-ol-derived compound of the invention with a further reaction shown for converting this molecule to the (R)-3-hydroxybutyrate analogue thereof.

Figure 3:
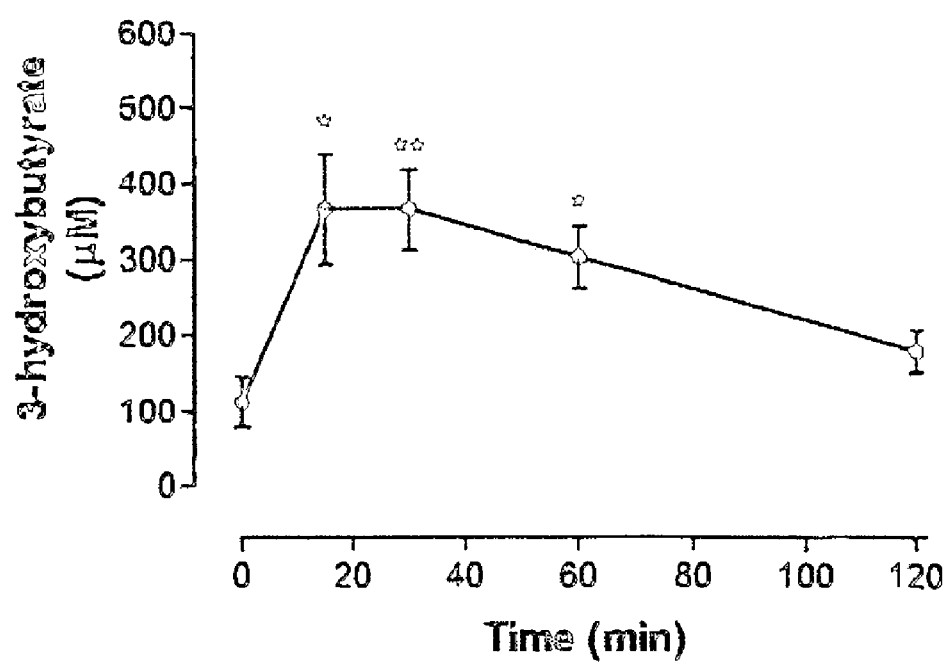

FIG. 3: Ketogenic effect of oral administration of the reference standard, KTX 0101 (sodium (R)-3-hydroxybutyrate), as determined by increases of β-hydroxybutyrate concentrations in rat plasma.

Figure 4:
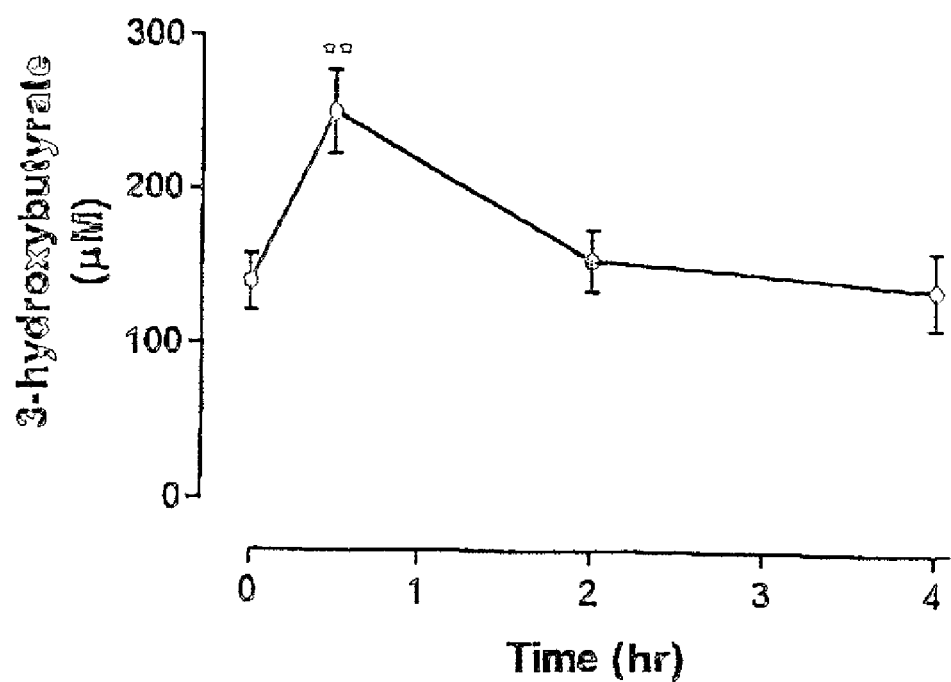

FIG. 4: Ketogenic effect of oral administration KTX 0204 (2-keto-butan-4-ol ester) as determined by increases of β-hydroxybutyrate concentrations in rat plasma

EXAMPLES

General Procedure for the Synthesis of R-3HB triolide from poly(3-hydroxybutyrate),PHB (FIG. 1).

A mixture of PHB (36 g) and toluene-4-sulphonic acid monohydrate (23 g) in 750 ml of toluene/dichloroethane (4:1) was heated and stirred at reflux at 120° C. for 20 hrs. The water was removed azeotropically using a Dean-Stark trap for 15 hrs The resulting clear brown solution was cooled to room temperature, washed with a half-saturated solution of $Na_2CO_3$, then washed with a saturated solution of NaCl, dried over $MgSO_4$, filtered and evaporated to dryness. The crude mixture was purified by column chromatography using silica gel as the stationary phase and an 8% hexane/ethylacetate mixture as the eluent followed by repeated crystallizations in hexane/ethylacetate. The yield of the purified product was 15 g (40%). Analysis of the product was as follows: melting point 110° C.; $^1$H NMR (300 MHz, $CDCl_3$): δ 1.30 (d, J=6.4 Hz, $CH_3$), 2.39 (dd, J=2.1, 11.3 Hz), 2.46 (dd, J=11.3, 13.5 Hz) and 5.31-5.39 (m, CH); $^{13}$C NMR (75.5 MHz, $CDCl_3$): δ 20.76 ($CH_3$), 42.16 ($CH_2$), 68.87 (CH) and 170.01 (CO).

EXAMPLE 1

Synthesis of KTX 0204 (2-keto-butan4-ol ester) Via the Lipase-catalyzed Ring Opening of (R)-3-hydroxybutyrate triolide Using 4-hydroxy-2-butanone as the Acyl Acceptor (FIG. 2)

The lipase-catalyzed ring-opening of (R)-3HB triolide using 2-keto-4-butanol (4-hydroxy-2-butanone) as the acyl acceptor was found to occur when performed in THF at 48° C. or 55° C. Although a number of lipases were found to be active for this transformation (Table 1), our work focused on the use of CAL-B. With CAL-B, the reaction was performed in THF for 72 hrs at 40° C.

Purified triolide (1 g, 3.88 mmol) was added into a round-bottom flask (50 ml) with 2-keto-4-butanol (683 mg, 7.8 mmol), anhydrous THF (20 ml), and CAL-B (536 mg, 30%-by-wt. relative to tote substrates). The product was visualized on thin layer chromatography (tlc) plates by converting its terminal hydroxyl group to the corresponding acetate derivative. This derivatization was performed on the tlc plate by first heating the plate with acetic anhydride followed by charring with CAM. The product was purified by column chromatography. The column was packed in pure chloroform and was eluted with methanol:chloroform, 1:49).

The product was a water-soluble syrup and the yield was 65%.

$^1$H NMR ($CDCl_3$): δ 1.20-1.31 (9H, m,J=6.4 Hz, $CH_3$), 2.19 (3H, s,$CH_3$), 2.41-2.81 (6H,m,$COCH_2$×3), 3.30 (1H,s, OH), 3.82-3.86 (1H,m,CH), 4.16-4.21 (1H,m,$COCH_6$) and 4.31-4.38 (3H,m,CH,$COCH_2$) and 5.30-5.26 (1H,m,CH).

$^{13}$C NMR ($CDCl_3$): δ 19.89, 22.47, 30.23 ($CH_3$), 59.39 (C-4), 43.28 (C-3), 42.84 (C-14), 42.09 (C-10), 40.66(C-6), 64.33(C-15), 67.57 (C-7,C-11), 172.03, 172.59 (CO) and 205.60 (CO).

CHN Analysis: Anal. Calcd. for $C_{16}H_{26}O_8$: C, 55.48; H, 7.57; O, 36.95. Found: C, 55.02; H,7.79; O, 37.19.

EXAMPLE 2

The use of Various Commercial Lipases to Catalyse the Synthesis of KTX 0204 (2-ketobutan-4-ol ester) Via the lipase-catalyzed Ring Opening of (R)-3-hydroxybutyrate Triolide Using 4-hydroxy-2-butanone as the Acyl Acceptor 4-Hydroxy-2-butanone was reacted with (R)-3-hydroxybutyrate triolide under a number of different conditions (Table 1). 4-Hydroxy-2-butanone is a small and active acyl acceptor using a wide range of lipases, including *Candida antarctica* lipase (CAL-B or Novozyme 435), *Pseudomonas cepecia* lipase (Amano Pharmaceuticals) and *Mucor miehei* lipase. The reactions between 4-hydroxyl-2-butanone and (R)-3-hydroxybutyrate triolide with the lipases, apart from CAL-B, were performed in tetrahydrofuran using a 48 hr incubation period at temperatures of both 40° C. and 55° C. The incubation time with CAL-B was 72 hrs at 40° C. and 55° C.

TABLE 1

Experimental variables and results for the ring-opening of (R)-3-hydroxybutyrate triolide by reaction with 4-hydroxyl-2-butanone using a lipase as the catalyst.

| Source of lipase enzyme | Solvent | Temperatures investigated (° C.) | Result |
|---|---|---|---|
| *Candida antarctica* lipase (CAL-B) (Novozym 435) | Tetrahydofuran (THF) | 40 and 55 | Positive reaction |
| CAL-B on Accurel ® support | THF | 40 and 55 | Positive reaction |
| *Pseudomonas cepecia* (PS.Amano) | THF | 40 and 55 | Positive reaction |
| *Mucor meihei* | THF | 40 and 55 | Positive reaction |

The reactions were conducted for 72 hrs for CAL-B and 48 hrs for the other lipases.

EXAMPLE 3

Ketogenic Effect of KTX 0204 (2-keto-butan-4-ol ester )

Male Sprague-Dawley rats (weight range 200-250 g) were obtained from Charles River, Margate, Kent. The rats were group housed in polypropylene cages at a temperature of 21 ±4° C. and 55 ±20% humidity and on a standard light/dark cycle. Animals had free access to a standard pelleted rat diet and tap water at all times. Animals were accustomed to these conditions for at least one week before experimentation.

KTX 0204 (2-keto butan-4-ol ester), which was mostly soluble in deionized water and produced a cloudy and stable solution, was administered by gavage at 300 mg/kg po. Control animals received the appropriate vehicle (deionized water at 1 ml/kg) via the same route. Data for KTX 0101 (sodium (R)-3-hydroxybutyrate) are shown for comparison.

Animals were killed by $CO_2$ and blood (approx, 5 ml) was collected by cardiac puncture at various times after dosing. Blood was collected into EDTA-coated plasma collection tubes (Sarstedt 5 ml K2E tubes) and kept on ice prior to centrifugation. Tubes were centrifuged in an Eppendorf 570R centrifuge at 4° C. for 5 minutes at 2500 rpm (1000 g). Following plasma separation, extreme care was taken to avoid contamination with red blood cells and samples were re-centrifuged as necessary. Plasma samples were initially frozen on dry ice and transferred to a −75° C. freezer until required for analysis.

| | Protocol for KTX 0204 only | | |
|---|---|---|---|
| Group | Number of animals | Time of blood sampling (min) | Treatment |
| A | 7 | 0 | Vehicle baseline |
| B | 4 | 30 | KTX 0204 (300 mg/kg po) |
| C | 4 | 120 | KTX 0204 (300 mg/kg po) |
| D | 4 | 240 | KTX 0204 (300 mg/kg po) |

| | Protocol for KTX 0101 only | | |
|---|---|---|---|
| Group | Number of animals | Time of blood sampling (min) | Treatment |
| A | 4 | 0 | Vehicle baseline |
| B | 4 | 15 | KTX 0101 (300 mg/kg po) |
| C | 4 | 30 | KTX 0101 (300 mg/kg po) |
| D | 4 | 120 | KTX 0101 (300 mg/kg po) |

Sodium DL-β-hydroxybutyrate (H-6501 Lot 111K2618) was obtained from Sigma. A stock solution of β-bydroxybutyrate (40 mM DL racemate equivalent to 20 mM D-isomer) was prepared in 0.9% saline solution, kept at 4° C. and used to generate appropriate dilutions for an assay standard curve. Such solutions have been shown to be stable for at least 2 months.

Commercial clinical assay kits for the determination of D-β-hydroxybutyrate were obtained from Random Laboratories (Antrim, UK). Kits were obtained in two pack sizes (Ranbut RB1007: 10×10 ml and RB1008: 10×50 ml) but were otherwise identical. Each kit contained a standard solution of 1 mM D-β-hydroxybutyrate that was assayed every time to confirm the assay was performing correctly. The kit relies on measuring the appearance of NADH via the activity of β-hydroxybutyrate dehydrogenase measured as an increase of OD340 nm. An alkaline pH is necessary to drive the reaction equilibrium towards the production of NADH and acetoacetate.

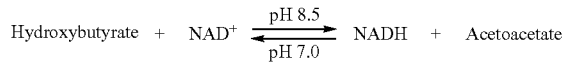

The protocol supplied with the Ranbut kits was for a discrete (cuvette-based) spectrophotometric assay, so the protocol was modified for suitability with a 96-well microplate format using blank, flat-bottomed microplates (Greiner PS 655101 Lot 98 35 01). Assays were performed in triplicate using a sample volume of 10 µl to each well for the standards and usually 20 µl for plasma samples (though this was varied for some experiments). Standard dilutions and samples were pipetted a single plate at a time and preincubated at 37° C. for 15 minutes in the sample compartment of a Molecular Devices VERSA$_{MAX}$ tunable microplate reader. The appropriate volume of assey reagent was reconstituted, according to instructions, using distilled water and preincubated at 37° C. for 15 minutes using a static water bath. The assay plate was ejected and the reaction started by adding rapidly 250 µl of reagent to each well (avoiding air bubbles). The plate was reloaded, mixed and then the change in OD340 nm followed in kinetic mode with a reading at every 15 seconds for a total of 2 minutes. The reaction rate was then determined from the OD increase over a suitable 1 minute period, after allowing a necessary period for the reaction rate to settle. The rate between 45 seconds and 105 seconds was used as the default measuring period, though occasionally a different period was used as necessary (e.g. if an aberrant reading was obtained at one of these time-points).

For analysis of spectrophotometric rate assays, linear regression analysis to the standard curve was used followed by interpolation of unknown values (GraphPad Prism 3.0) For comparison of treatment groups with vehicle, multiple 2-tailed T-tests were used and $p<0.05$ was taken to indicate statistical significance.

KTX 0101 (sodium (R)-3-hydroxybutyrate): After oral administration at 300 mg/kg (po), the sodium salt of (R)-3-hydroxybutyrate rapidly increased plasma concentrations of β-hydroxybutyrate (FIG. 3). The maximum increase was 0.4 mM observed at 15 min ($P<0.05$), it plateaued at this level until 30 min ($P<0.01$) and declined thereafter. The level β-hydroxybutyrate was still significantly ($P<0.05$) elevated at 1 h, but it returned to control values by 2 h.

KTX 0204 (2-keto-butan-4-ol ester): After oral administration at 300 mg/kg (po), the 2-keto-butan-4-ol ester of (R)-3-hydroxybutyrate triolide rapidly increased plasma concentrations of β-hydroxybutyrate (FIG. 4). The maximum increase of 0.25 mM observed at 30 min. was not quite so large as that produced by the equivalent oral dose of sodium (R)-3-hydroxybutyrate, but the change was nevertheless highly significant ($P<0.0$ 1). The plasma concentration of β-hydroxybutyrate declined thereafter and had returned to control values by 1 hr.

The invention claimed is:

1. A compound of general formula

wherein n is an integer of 3 to 10, A is the residue of a 3-keto-alkan-1-ol remaining after that 3-keto-alkan-1-ol is esterified with the oligomer R(OCH(CH$_3$)CH$_2$C(O))$_n$—OH and R is selected from the group consisting of H, C$_1$-C$_6$ alkyl and acetoacetyl.

2. A compound as claimed in claim 1 wherein A is a residue is of 4-hydroxy-2-butanone.

3. A compound as claimed in claim 1 which is a 4-hydroxy-2-butanone ester of an (R)-3-hydroxybutyrate oligomer having general formula

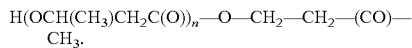

4. A compound as claimed in claim 1 wherein n is an integer of 3 to 5.

5. A compound as claimed in claim 1 wherein n is 3.

6. A nutraceutical or pharmaceutical composition comprising a compound as claimed in claim 1 together with a foodstuff or beverage component or a pharmaceutically acceptable carrier, diluent or excipient.

7. A nutraceutical composition as claimed in claim 6 wherein the composition comprises a component of a beverage, which includes liquid, semi-solid or gelled preparations, or a component of a foodstuff, which also includes an edible oil, emulsion, gel or solid.

8. A method of treating a human or animal in need of treatment of a disease or medical condition by production of a physiologically acceptable ketosis comprising administering to the patient a therapeutically effective amount of a compound of claim 1.

9. A method as claimed in claim 8 wherein the amount of compound is sufficient to raise the patients' blood ketone levels to between 0.2 to 20 mM.

10. A method for the manufacture of a compound as described in claim 1 comprising reacting a cyclic oligomer of (R)-3-hydroxybutyrate containing between 3 and 10 (R)-3-hydroxybutyrate moieties with a 3-keto-alkan-1-ol in an organic solvent in the presence of a lipase.

11. A method as claimed in claim 10 wherein the solvent is a furan or pyran solvent.

12. A method as claimed in claim 10 wherein lipase is selected from *Candida antarctica* lipase-type B, *Pseudomonas cepecia* (PS; Amano Pharmaceuticals) and *Mucor methei* lipase.

13. A method as claimed in claim 10 wherein n is 3, A is a 4-hydroxy-2-butanone residue, R is H, the cyclic oligomer is (R)-3-hydroxybutyrate triolide, the alcohol is 4-hydroxy-2-butanone, the solvent is tetrahydrofuran and the lipase is *Candida antarctica* lipase-type B.

14. A method as claimed in claim 8 wherein the treatment is for acute trauma, hemorrhagic shock, neurodegeneration, diabetes, and epilepsy, stroke, head trauma, myocardial infarction, congestive heart failure, pulmonary failure, kidney failure, obesity depression, pain and impaired cognition.

* * * * *